United States Patent [19]

Osbourn et al.

[11] Patent Number: 5,994,519
[45] Date of Patent: Nov. 30, 1999

[54] LABELLING AND SELECTION OF MOLECULES

[75] Inventors: Jane Katharine Osbourn, Cambridge; Elaine Joy Derbyshire, Royston; John Gerald McCafferty, Babraham; Tristan John Vaughan, Cambridge; Kevin Stuart Johnson, Caldecote Highfields, all of United Kingdom

[73] Assignee: Cambridge Antibody Technology Limited, Cambridgeshire, United Kingdom

[21] Appl. No.: 08/889,291

[22] Filed: Jul. 8, 1997

[30] Foreign Application Priority Data

| Jul. 8, 1996 | [GB] | United Kingdom | 9614292 |
| Nov. 29, 1996 | [GB] | United Kingdom | 9624880 |
| Jun. 18, 1997 | [GB] | United Kingdom | 9712818 |

[51] Int. Cl.$^6$ .................................................. G01N 33/53
[52] U.S. Cl. ............................................................ 530/413
[58] Field of Search ........................... 435/7.1, 7.2, 7.75, 435/5; 530/412, 413

[56] References Cited

U.S. PATENT DOCUMENTS

| 5,583,001 | 12/1996 | Bobrow et al. ........................... 435/7.5 |
| 5,731,158 | 3/1998 | Bobrow et al. ........................... 435/7.5 |

FOREIGN PATENT DOCUMENTS

| 0 120 694 A2 | 10/1984 | European Pat. Off. . |
| 0 125 023 A1 | 11/1984 | European Pat. Off. . |
| 0 184 187 A2 | 6/1986 | European Pat. Off. . |
| 0 239 400 A2 | 9/1987 | European Pat. Off. . |
| 0 239 400 B1 | 9/1987 | European Pat. Off. . |
| 0 465 577 B1 | 1/1992 | European Pat. Off. . |
| 0 260 280 | 5/1992 | European Pat. Off. . |
| 2 188 638 | 10/1987 | United Kingdom . |
| WO 90/11523 | 10/1990 | WIPO . |
| WO 92/01047 | 1/1992 | WIPO . |
| WO 93/11161 | 6/1993 | WIPO . |
| WO 94/13804 A1 | 6/1994 | WIPO . |

OTHER PUBLICATIONS

Lenstra et al., "Mapping of viral epitopes with prokaryotic expression products", Arch Virol 110:1–24, 1994.

Kricka, "Selected strategies for improving sensitivity and reliability of immunoassays", Clinical Chemistry 40:347–357, 1994.

Adams, J.C., "Biotin Amplification of Biotin and Horseradish Peroxidase Signals in Histochemical Stains," *Journal Histochemistry and Cytochemistry*, 40(10):1457–1463 (1992).

Altschul, S.F. et al., "Basic Local Alignment Search Tool," *Journal of Molecular Biology*, 215:403–410 (1990).

Bird, R.E. et al., "Single–Chain Antigen–Binding Proteins," *Science*, 242:423–426 (Oct., 1988).

Bobrow, M.N. et al., "Catalyzed reporter deposition, a novel method of signal amplification," *Journal of Immunological Methods*, 125:279–285 (1989).

Boublik, Y. et al., "Eukaryotic Virus Display: Engineering the Major Surface Glycoprotein of the Autograph californica Nuclear Polyhedrosis Virus (AcNPV) for the Presentation of Foreign Proteins on the Virus Surface," *BioTechnology*, 13:1079–1084 (Oct., 1995).

Clackson, T. et al., "In vitro selection from protein and peptide libraries," *Trends Biotechnology*, 12:173–184 (1994).

Diamond, R.H. et al., "Novel Delayed–early and Highly Insulin–induced Growth Response Genes," *Journal of Biological Chemistry*, 268(20):15185–15192 (Jul., 1993).

Fields, S. et al., *Nature*, "A novel genetic system to detect protein–protein interactions," 340:245–246 (Jul., 1989).

Fisch, I. et al., "A strategy of exon shuffling for making large peptide repertoires displayed on filamentous bacteriophage," *Proc. Natl. Acad. Sci., USA*, 93:7761–7766 (Jul., 1996).

Griffiths, A.D. et al., "Human anti–self with high specificity from phage display libraries," *EMBO J.*, 12(2):725–734 (1993).

Holliger, P. et al., ""Diabodies": Small bivalent and bispecific antibody fragments," *Proc. Natl. Acad. Sci., USA*, 90:6444–6448 (Jul., 1993).

Huston, J.S. et al., "Protein engineering of antibody binding sites: Recovery of specific activity in an anti–digoxin single–chain Fv analogue produced in *Escherichia coli,*" *Proc. Natl. Acad. Sci., USA*, 85:5879–5883 (Aug., 1988).

(List continued on next page.)

Primary Examiner—Donna C. Wortman
Assistant Examiner—Brenda G. Brumback
Attorney, Agent, or Firm—Marshall, O'Toole, Gerstein, Murray & Borun

[57] ABSTRACT

A method of labelling molecules which includes providing in a common medium a label molecule, a marker ligand able to bind a member of a specific binding pair, such as an antigen, a sbp member, an enzyme able to catalyse binding of the label molecule to other molecules, the enzyme being associated with the marker ligand; causing or allowing binding of the marker ligand to the sbp member; and causing or allowing binding of the label molecule to other molecules in the vicinity of the marker ligand bound to the sbp member. The marker ligand may be an antibody or any specific binding molecule, such as a chemokine or cytokine. A complementary member of the specific binding pair may be included, e.g. an antibody, or a diverse population of such sbp members, e.g. antibodies, may be included within which those which bind the counterpart sbp member, e.g. antigen, may be labelled and subsequently isolated for manipulation and/or use. Suitable labels include biotin-tyramine with signal transfer being catalysed by hydrogen peroxidase. Cells, virus particles and other moieties may be labelled, for identification or obtention of proteins which interact or are in close proximity with a particular sbp member, or of cells of interest, or for enhancement of labelling, e.g. for cell sorting.

19 Claims, 8 Drawing Sheets

OTHER PUBLICATIONS

Jespers, L.S. et al., "Surface Expression and Ligand–Based Selection of cDNAs Fused to Filamentous Phage Gene VI," *BioTechnology,* 13(4):378–382 (1995).

Lu, Z. et al., "Expression of Thioredoxin Random Peptide Libraries on the *Escherichia coli* Cell Surface as Functional Fusions to Flagellin: A System Designed for Exploring Protein–Protein Interactions," *BioTechnology,* 13(4):366–372 (Apr., 1995).

Marks, J.D. et al., "By–passing Immunization Human Antibodies from V–gene Libraries Displayed on Phage," *J. Molecular Biology,* 222:581–597 (1991).

Munro, S. et al., "An Hsp70–like Protein in the ER: Identity with the 78 kd Glucose–Regulated Protein and Immunoglobulin Heavy Chain Binding Protein," *Cell,* 46:291–300 (Jul., 1986).

Osuna, J. et al., "Microbial Systems and Directed Evolution of Protein Activities," *Critical Reviews in Microbiology,* 20(2):107–116 (1994).

Sugiyama, Y. et al., "Systemic production of foreign peptides on the particle surface of tobacco mosaic virus," *FEBS Letters,* 359:247–250 (1995).

Vaughan, T.J. et al., "Human Antibodies with Sub–nanomolar Affinities Isolated from a Large Non–immunized Phage Display Library," *Nature Biotechnology,* 14:309–314 (Mar., 1996).

Ward, E.S. et al., "Binding activities of a repertoire of single immunoglobulin variable domains secreted from *Escherichia coli,"* *Nature,* 341:544–546 (Oct. 12, 1989).

Bobrow, M.N. et al., "Catalyzed reporter deposition, a novel method of signal amplification, II. Application to membrane immunoassays," *J. Immunological Methods,* 137:103–112 (1991).

Figure 1 : Biotinylation of proteins around the site of HRP activity

HRP = Hydrogen peroxidase

BT = Biotin tyramine

CEA = Carcinoembryonic antigen

Figure 8

LABELLING AND SELECTION OF MOLECULES

The present invention relates to labelling and selection of molecules, such as members of a specific binding pair (sbp) able to bind a complementary sbp member of interest, especially though not exclusively a complementary sbp member for which an existing ligand is available. In exemplary embodiments, the present invention relates to selection of antibodies, or polypeptides comprising an antibody antigen binding domain, specific for an antigen of interest for which an existing binding molecule, which may be an antibody, such as a monoclonal antibody, is already available It involves deposition of a label or reporter molecule, such as biotin-tyramine, on molecules in the vicinity of a "marker ligand" which comprises for example a monoclonal antibody (specific for an antigen of interest) in association with an enzyme which catalyzes such deposition. Molecules labelled in accordance with the present invention may include binding members such as antibodies which bind the same binding target (e.g. antigen) as the marker ligand if such binding members are included in the reaction medium, the target molecule to which the marker ligand binds, which allows for identification and/or purification of unknown antigen targets, and/or other molecules in the vicinity of the binding target and/or the marker ligand when bound to its binding target, e.g. on a cell surface on which the binding target is found, including molecules complexed with the binding target, allowing for identification of novel protein-protein interactions. There are also various advantages in labelling cells or other particles using the present invention, especially when the process is reiterated to augment the extent of labelling. Further aspects and embodiments of the invention are disclosed herein.

Numerous kinds of specific binding pairs are known, as epitomised by the pair consisting of antibody and antigen. Other specific binding pairs are discussed briefly infra and may equally be employed in the various aspects of the present invention disclosed herein. For convenience, however, most of the discussion herein refers to "antibody" as the type of (first) specific binding pair (sbp) member whose selection is sought in performance of methods of various embodiments of the invention, "antigen" as the complementary (second) sbp member of interest for which specific binding molecules may be sought to be selected and "marker ligand" as the pre-existing binding molecule known to be able to bind the complementary sbp member of interest. Generally, the marker ligand comprises an antibody antigen binding domain specific for the complementary sbp member of interest (e.g. antigen). Other suitable marker ligands include hormones, cytokines, growth factors, neuropeptides chemokines, enzyme substrates and any other specific binding molecule. Also present is a label or reporter molecule and an enzyme that catalyses binding of the label to other molecules in the vicinity.

Bearing this in mind, the present invention (in some embodiments) can be said to have resulted from the inventors having identified a means to select for antibodies binding to an antigen, e.g. on cell surfaces, other solid supports, or in solution, using a marker ligand for the antigen to guide the recovery of antibodies binding in proximity to the marker ligand. This provides means to label molecules which bind in close proximity to a given defined ligand by transfer of a reporter molecule or label to the binding molecules. The defined ligand occupies a specific epitope on the antigen and generally blocks that particular epitope, and epitopes overlapping it, from binding other antibodies. Thus, antibodies which are selected for are usually those which do not bind to the marker ligand epitope, but are those which bind neighbouring epitopes. Antibodies which bind the same epitope as the original marker ligand may be obtained by an iterative process—using an antibody obtained in one round of the process as a second marker ligand in a further round—or by using appropriate conditions, as discussed further below.

Signal transfer selection may be used to generate antibodies which bind to the same epitope as the marker ligand by re-iterating the selection procedure. Antibodies selected from the first round of signal transfer selection may be used as new marker ligands for a subsequent round of selection which is carried out in the absence of the original marker ligand. This may be referred to as a "step-back" selection and may be used to select for antibodies which inhibit the original ligand binding. If the second stage of a step-back selection is carried out in the presence of the original marker ligand antibodies which bind the marker ligand-receptor complex, but not the receptor alone, may be selected. Such antibodies may be ligand agonists or antagonists. Of course, step back selection need not be limited to selection from antibody libraries; any pair of specific binding members can be used in such a procedure.

Antibodies which bind epitopes which are nearest to that bound by the marker ligand have the highest probability of becoming labelled, and the probability of labelling decreases with distance from the marker ligand epitope. Advantageously, the present invention may expedite the purification of such labelled molecules.

Transfer of the biotin tyramine reporter molecule may occur within up to about 25 nm according to experimental results infra. The distance from the binding site of the original marker ligand may be increased by iteration of the signal transfer process, or by adapting the guide molecule by the addition of a spacer between the guide molecule and the enzyme which catalyses the signal transfer. Such a spacer may be a chemical linker, polymer, peptide, polypeptide, rigid bead, phage molecule, or other particle.

Such a spacer may be of any suitable desired length, including about 10–20 nm, about 20–40 nm, about 40–60 nm, about 60–100 nm, about 100 nm or more, such as about 500 nm or more up to about 1 $\mu$m or more.

Furthermore, the labelling and subsequent purification of binding molecules specific for antigen of interest which are displayed on the surface of bacteriophage or other biological particles (see e.g. WO92/01047) facilitates recovery of nucleic acid encoding the specific binding molecules. In so-called "phage display", a binding molecule, e.g. antibody or antibody fragment, peptide or polypeptide, e.g. enzyme, is displayed on the surface of a virus particle which contains nucleic acid encoding the displayed molecule. Following selection of particles that display molecules with the desired binding specificity, the nucleic acid may be recovered from the particles and used to express the specific binding molecules or derivatives thereof, which may then be used as desired.

Other display systems may be used instead of display on filamentous bacteriophage. Such systems include display on whole bacterial cells or modified bacterial surface structures (Osuna et al. *Crit. Rev. Microbiol.*, 1994, 20: 107–116; Lu et al., *BioTechnology*, 1995, 13: 366–372) and eukaryotic viruses (Boublik et al. *BioTechnology*, 1995, 13: 1079–1084; Sugiyama et al., *FEBS Lett.*, 1995, L 359: 247–250). Bacteriophage display libraries may be generated using fusion proteins with the gene III protein (e.g. Vaughan et al. *Nature Biotechnology*, 1996, 14: 309–314), or the major gene VIII coat protein (Clackson and Wells, *Trends Biotechnol.*, 1994, 12: 173–184), or the gene VI protein (Jespers et al., *BioTechnology*, 1995, 13: 378–382).

Herein it is shown that antibodies binding specifically to a given target antigen, e.g. expressed on the surface of cells, may be selected from a large, diverse phage display library using an existing ligand of the desired antigen to guide the selection. It is also demonstrated that the desired antigen can be purified from the cells by chemical modification of the antigen in a reaction catalysed by the existing ligand. Antibodies to any antigen for which a known ligand exists may be obtained in this way, as may antibodies which bind specifically to the antigen-ligand complex rather than the antigen alone. In addition existing ligands to unknown molecules (e.g. antigens) may be used as markers to guide selection of antibodies to the unknown molecule or purification of the unknown molecule itself. Surface accessible regions of an antigen may be identified by means of their accessibility to labelling, e.g. biotinylation. Biotinylated molecules may be cleaved, e.g. proteolytically if they are peptidyl in nature, and biotinylated fractions detected, e.g. following size fractionation. Furthermore, the labelling of other molecules in the vicinity of the molecule to which the marker ligand binds allows for those other molecules to be identified and/or purified for further study. It also allows for particular moieties on which the binding target appears to be identified and/or purified, for instance one cell type displaying a particular antigen from among a complex mix of different cell types. Determination of the extent of labelling which occurs in the vicinity of a the molecule to which the marker ligand binds may be used to determine the copy number of that molecule, e.g. on a cell surface.

Selection of molecules in accordance with the present invention is not limited to antigens on cell surfaces. For example, complex proteins with multiple domains or subunits may be coated onto a solid support and ligands specific for a particular domain or subunit may be used as marker ligands to guide selection of antibodies to other neighbouring domains or subunits. A domain or subunit may be conjugated, directly or indirectly, to the enzyme (e.g. HRP) and domain-domain or subunit-subunit interactions used to guide selection. This may be termed "domain walking". Marker ligands specific for particular epitopes on a protein may also be used to guide he selection away from the marker ligand epitope and to select for binding molecules which bind other epitopes within he radius of labelling (e.g. about 25 nm for biotinylation). his may be termed "epitope walking", and example of which is given in Example 8. A "step-back" selection may be carried out (as discussed elsewhere herein), generating a sbp member with the same or overlapping epitope specificity as the original marker ligand.

Techniques of the present invention for selection of molecules, which may be known as "signal transfer selection", need not be limited to antibody selection; selection from peptide libraries (e.g displayed on phage) may be used to identify peptides with specific binding characteristics for a given protein, which may be any binding domain or type of ligand interaction, not just antibody/epitope. Example 14 illustrates this using peptide libraries to epitope map an antibody (conjugated to HRP) in solution. Libraries or diverse populations of proteins other than antibodies may be displayed on the surface of phage to allow isolation of novel proteins which bind to a protein in proximity to the marker ligand.

Signal transfer selection may also be used to chemically modify a particular cell type possessing a specific antigen to facilitate purification of that cell type from a background of other cells. Signal transfer selection may also be applied to the humanisation of existing monoclonal antibodies since Mab's which recognise an undefined antigen may be used to target selection of human antibodies with a similar binding capacity. This may involve the marker ligand including the binding domain of a non-human antibody, such as a mouse monoclonal antibody, which may be conjugated directly or indirectly to an enzyme such as HRP. Signal transfer selection may be used to obtain antibodies from a human antibody library displayed on the surface of a suitable virus, such as bacteriophage or retrovirus, or other biological particle, which bind to the same antigen as the pre-existing non-human antibody. Repeating the process ("step-back") using an antibody obtained in a first performance of the process as the marker ligand in a further performance of the process may be used to obtain human antibodies which bind to the same epitope as the original non-human antibody—a humanised antibody. Ability of two binding molecules such as antibodies to bind the same epitope may of course be assessed using an appropriate competition assay.

Signal transfer selection may be used to generate two antibodies, or other binding members, which bind adjacent epitopes on the same target molecule. This provides the potential to generate bispecific antibodies (such as "diabodies") which may have higher affinities or other desirable biological properties (e.g. neutralising ability) which the individual antibodies alone do not exhibit. Signal transfer selection may also be used with enzyme substrates to direct selection of antibodies which bind enzyme active sites and which may be enzyme inhibitors or activators. Direct biotinylation of the enzyme active site by the substrate may provide a tool to map amino acid residues important in catalysis.

A local supply of hydrogen peroxide or other free radical precursor may be generated by coupling the marker ligand to an enzyme which produces the substrate for the free-radical generating enzyme, such as HRP, for example, glucose oxidase or superoxide dismutase. This enables the local generation of radicalised biotin-tyramine or other label molecule in the vicinity of the free-radical generating enzyme. An active form of free-radical generating enzyme may be generated in response to a binding event, such as the bringing together of two subunits of the enzyme to produce an active enzyme, or bringing together an activator of the enzyme with the enzyme itself. Radicalised label molecule such as biotin-tyramine may be thus generated in response to binding events, which may be between specific cell types, proteins, or other specific binding members.

TERMINOLOGY

Specific binding member

This describes a member of a pair of molecules which have binding specificity for one another. The members of specific binding pair may be naturally derived or synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other.

Examples of types of specific binding pairs are antigen-antibody, biotin-avidin/streptavidin, hormone-hormone receptor, receptor-ligand, enzyme-substrate.

Antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject co genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Antigen binding domain

This describes the part of an antibody which comprises the area which specifically binds to and is complementary to part or all of an antigen. Where an antigen is large, an antibody may only bind to a particular part of the antigen, which part is termed an epitope. An antibody antigen binding domain may be provided by one or more antibody variable domains. Preferably, an antigen binding domain comprises an antibody light chain variable region (VL) and an antibody heavy chain variable region (VH).

Specific

This refers to the situation in which one member of a specific binding pair will not show any significant binding to molecules other than its specific binding partner (e.g. an affinity of about 1000× worse). The term is also applicable where eg an antigen binding domain is specific for a articular epitope which is carried by a number of antigens, in which case the specific binding member carrying the antigen binding domain will be able to bind to the various antigens carrying the epitope.

Functionally equivalent variant ford

This refers to a molecule (the variant) which although having structural differences to another molecule (the parent) retains some significant homology and also at least some of the biological function of the parent molecule, e.g. he ability to bind a particular antigen or epitope. variants may be in the form of fragments, derivatives or mutants. A variant, derivative or mutant may be obtained by modification of the parent molecule by the addition, deletion, substitution or insertion of one or more amino acids, or by the linkage of another molecule. These changes may be made at the nucleotide or protein level. For example, the encoded polypeptide may be a Fab fragment which is then linked to an Fc tail from another source. Alternatively, a marker such as an enzyme, flourescein, etc, may be linked.

Marker ligand

This refers to one member of a specific binding pair able to bind complementary sbp member. In embodiments of the present invention, it is used to guide catalysis of label or reporter molecule deposition at and around its site of binding to the complementary other member of the specific binding pair.

According to a first aspect of the present invention there is provided a method of labelling molecules, the method including providing in a common medium:
a label molecule;
a ligand ("first marker ligand") able to bind a second member of a specific binding pair (sbp);
a said second sbp member;
an enzyme able to catalyse binding of said label molecule to other molecules, said enzyme being associated with said first marker ligand;
causing or allowing binding of said first marker ligand to said second sbp member; and
causing or allowing binding of said label molecule to other molecules in the vicinity of said first marker ligand bound to said second sbp member.

A first member of a specific binding pair, such as an antibody, may be included, or a diverse population of such first sbp members including one or more which bind the second sbp member. Molecules to which the label molecule binds may include a sbp member ("first sbp member") which binds said second sbp member.

Molecules to which the label molecule binds may include a sbp member ("first sbp member") which binds a molecule in the vicinity of said second sbp member, as discussed further infra.

In preferred embodiments of the invention the first sbp member is a polypeptide comprising an antibody antigen binding domain, and the second, complementary sbp member is antigen. The marker ligand may be a polypeptide comprising an antibody antigen binding domain, such as a monoclonal antibody or cloned scFv, Fab or other antibody fragment.

In a preferred embodiment of the present invention, the first member of the-specific binding pair is included and is labelled by binding of the label molecule. This allows identification and/or isolation of target molecules such as antibodies able to bind a substance of interest, such as antigen. (The term "target molecules" may be used to refer to molecules the identification of which is the object of the person skilled in the art operating the invention.) Such isolation may be facilitated if the label itself is a member of a specific binding pair. A preferred label exemplified herein is biotin, able specifically to bind avidin and streptavidin. Also exemplified is the use of light-activatible streptavidin as the label.

Following binding of a sbp member label such as biotin to a target sbp member (e.g. antibody), specific binding of the label to its complementary sbp member (e.g. streptavidin in the case of biotin labelling) may be used in isolation of the target sbp member. For instance, streptavidin-coated magnetic beads may be added to the medium or milieu, allowing streptavidin-biotin binding to take place, then extracted using a magnet. Sbp members labelled with biotin may then be recovered from the beads.

Other suitable labels include photo-reactive compounds such as N-[N-4-azido-tetraflurobenzoyl)-biocytinyloxy]-succinimide, or photoreactive crosslinking agents such as sulfor-SANPAH or SAND (sulfosuccinimidyl 2-[m-azido-o-nitrobenzamido]-ethyl-1,3-dithiopropionate) in combination with streptavidin or biotin. Conveniently, biotin or other label is conjugated to tyramine, whose covalent binding to peptide molecules is catalysed by oxygen free radicals generated by hydrogen peroxidase in the presence of hydrogen peroxide. Instead of biotin-tyramine, labelling in performance of the present invention may employ other forms of modified tyramine including fluoresceinated tyramine or other free radical reagents, such as p-hydroxyphenylpropionyl-biocytin and biotynil-coumarin galactose. Labels such as biotin (e.g. as biotin-tyramine) may be preferred over photo-reactive labels, e.g. because of ease of handling, though Example 10 below demonstrates operation of the present invention using a label whose binding is light-activated, i.e. SAND linked to streptavidin. An advantage of using a light-activatable label, such as streptavidin-SAND, is the distance over which this label can be deposited. The linker between the streptavidin and SAND is 1.8 nm so the proximity within which the streptavidin is deposited is up to a maximum of about 1.8 nm, compared with a radius of up to about 25 nm of biotinylation which is obtainable with biotin-tyramine.

The enzyme that catalyses binding of the label molecule to other molecules may be associated with the marker ligand by any suitable means available in the art. It may be conjugated directly, e.g. via a peptide bond (in which case a fusion protein comprising marker ligand and enzyme may be produced by expression from encoding nucleic acid), or by chemical conjugation of the marker ligand and enzyme, or indirectly. Indirect conjugation of enzyme and marker ligand may conveniently be achieved using a further binding molecule that forms a specific binding pair with the marker ligand. For example, the marker ligand may be a mouse monoclonal antibody, or may comprise a mouse antibody sequence, and the enzyme may be provided conjugated to an anti-mouse antibody or antibody antigen binding domain (e.g. as a fusion protein). Binding of anti-mouse antibody to the mouse monoclonal, itself binding the antigen of interest (second sbp member), brings the conjugated enzyme into close proximity with the antigen and any molecules in the medium or milieu able to bind the antigen (e.g. target antibodies), allowing the enzyme to catalyse labelling of such molecules (e.g. target antibodies) and/or the antigen. Labelled molecules may be identified and/or isolated for investigation and/or use.

As mentioned already, the first sbp member when provided in the reaction milieu may be one of a diverse population of that type of sbp member with different binding specificities. Such a population may be provided by expression from a genetically diverse repertoire of nucleic acid sequences. In the case of antibody antigen binding domains, these may be provided by expression from a repertoire of rearranged or unrearranged immunoglobulin sequences from an organism (preferably human) which has or has not been immunised with the antigen of interest. A repertoire of sequences encoding antibody antigen binding domains (VH and/or VL) may additionally or alternatively be provided by any of artificial rearrangement of V, J and D gene segments, mutation in vitro or in vivo, in vitro polynucleotide synthesis and/or any other suitable technique available in the art. Suggested references include Vaughan et al., (1996) *Nature Biotechnology* 14: 309–314; Griffiths et al., (1993) *EMBO J.* 12: 725–734.

Conveniently, a diverse population of binding molecules is provided displayed on the surface of a biological particle such as a virus, e.g. bacteriophage, each particle containing nucleic acid encoding the binding molecule displayed on its surface. WO92/01047 discloses in detail various formats for "phage display" of polypeptides and peptide binding molecules, such as antibody molecules, including scFv, Fab and Fv fragments, and enzymes, both monomeric and polymeric. Following labelling of phage displaying a target sbp member able to bind complementary sbp member of interest, and isolation of these from the reaction medium or milieu as discussed, nucleic acid may be recovered from phage particles. This nucleic acid may be sequenced if desired.

Other display systems, e.g. on bacterial cells or retroviruses, are applicable, as has been mentioned already.

The nucleic acid taken from the particle, or its nucleotide sequence, may be used to provide nucleic acid for production of the encoded polypeptide or a fragment or derivative thereof in a suitable expression system, such as a recombinant host organism. A derivative may differ from the starting polypeptide from which it is derived by the addition, deletion, substitution or insertion of amino acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, flouresceins etc may be linked to eg Fab, scFv fragments.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols In Molecular Biology*, Second Edition, Ausubel et al. eds., John Wiley & Sons, 1992. The disclosures of Sambrook et al. and Ausubel et al. are incorporated herein by reference.

The expression end product may be used to prepare a composition comprising the expression end product or a derivative thereof and optionally one or more further components such as a pharmaceutically acceptable vehicle, carrier or excipient, which may for example be used as a therapeutic or prophylactic medicament or a diagnostic product.

In some embodiments of the present invention, the second sbp member (to which the marker ligand binds—e.g. antigen) is labelled. This is useful if the target molecule is an unknown antigen/receptor for the known marker ligand (e.g. monoclonal antibody or the natural ligand for the antigen/receptor). In such case, the first sbp member may be omitted from the reaction medium or milieu. Following labelling of the second sbp member it may be identified and/or isolated in accordance with procedures disclosed herein.

According to a further aspect of the present invention there is provided reaction medium or milieu containing:
 a member of said specific binding pair;
 a label molecule;
 a ligand ("marker ligand") able to bind said sbp member;
 an enzyme able to catalyse binding of said label molecule to other molecules, said enzyme being associated with said marker ligand;
as provided in methods according to the invention. A further sbp member (designated "first") may be present, in which case the marker ligand is able to bind complementary "second" sbp member.

A further aspect of the present invention provides a sbp member identified as having ability to bind complementary sbp member of interest and/or isolated using a method as disclosed herein, including a receptor or ligand identified and/or isolated as disclosed, and compositions comprising such an identified and/or isolated sbp member and nucleic acid encoding the identified and/or isolated sbp member.

The present invention generally provides for any specific binding member identified by virtue of its ability to bind to complementary sbp member in close proximity (e.g. less than about 25 nm, and possibly less than about 20 nm, less than about 15 nm, less than about 10 nm, about 5–10 nm or about 5 nm) to an existing defined ligand, which may be termed a "marker ligand" and is used to guide catalysis of reporter molecule deposition on to the specific binding member.

The invention also provides for the use of the methods and means provided herein for the selection of phage-displayed sbp members, e.g. antibodies, peptides or proteins, also the selection or identification of unknown receptors using a known ligand, either by directed labelling of the receptor, or by production of an antibody against the receptor, followed by immuno-purification.

The invention also provides for the use of signal transfer selection in an iterative manner, i.e. using one or more sbp members selected in a cycle to select for further sbp members. This may be used to select sbp members which are capable of acting as antagonists or agonists to the original marker ligand used in the first stage of the selection.

Cell-surface or other receptors may be identified in a process according to the present invention by conjugating a ligand for the uncharacterised receptor (e.g. the natural of the receptor) with an enzyme able to catalyse binding of the label molecule. Binding of the ligand to the receptor, e.g. on cells expressing it, may then be carried out in the presence or absence of sbp members, such as antibodies, particularly a library of sbp members, e.g. displayed on phage, and the label molecule. The natural ligand may transfer the signal molecule directly onto the unknown receptor. Labelled receptor may then be directly purified, e.g. from a cell extract, and may be protein sequenced. In the presence of the sbp members, e.g. a library of antibodies displayed on phage, signal transfer will generate labelled sbp members which are able to bind the receptor. These may then be used to generate purified receptor by affinity purification.

The invention also provides for the use of such processes to identify unknown ligands for known receptors, either by directed labelling of the ligand, or by production of an antibody directed against the ligand followed by immuno-purification.

Further provided by the invention is the use of signal transfer selection to guide the selection of antibodies to a given epitope, domain or subunit of a protein or complex by an existing ligand or antibody which recognises a neighbouring epitope, domain or subunit. Existing sbp's (e.g. monoclonal antibodies) to a defined but perhaps undesirable epitope, subunit or region of a protein complex may be conjugated to an enzyme capable of catalysing binding of the label molecule to other molecules. These conjugated sbp's may then be used to direct signal transfer of the label to other sbp members, e.g. antibodies (e.g. on phage), binding to the same antigen but at non-identical, non-overlapping, but neighbouring epitopes which may be on adjacent subunits of a protein, or on adjacent regions of a protein complex.

Signal transfer selection may be used to obtain antibodies or other binding molecules which bind to the same epitope as the marker ligand. For example, sub-saturating amounts of the marker ligand may be added to a mutlimeric protein and the marker ligand may then direct selection of binding specificities recognising the same epitope as the marker ligand, but on a neighbouring subunit, or copy of the multimer. The marker ligand may be capable of labelling binding species which bind to the same epitope if labelling occurs concomitantly with the marker ligand being competed off the target protein by the species which is being selected for. Another application of the process is that of selecting for antibodies or other ligands which bind to a particular cell structure or cell type.

Further aspects of the present invention arise from the gene cloning work described in Example 16. Encoding nucleic acid, isolated polypeptides, specific binding molecules for the polypeptide and other molecules which interact with the polypeptide, particularly those which modulate its function, e.g. interfere with its association with CC-CKR5 and/or other polypeptide in the vicinity of CC-CKR5 on the surface of CD4+cells, other molecules which interact with the polypeptide, and methods and uses of these are all provided by the present invention.

Nucleic acid according to this aspect of the present invention may include or consist essentially of a nucleotide sequence encoding a polypeptide which includes an amino acid sequence shown in FIG. 8.

The coding sequence may be that shown in FIG. 8, or it may be a mutant, variant, derivative or allele of the sequence shown. The sequence may differ from that shown by a change which is one or more of addition, insertion, deletion and/or substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 8 yet encode a polypeptide with the same amino acid sequence. The polypeptide may include a sequence of about 60 contiguous amino acids from FIG. 8, more-preferably about 70 contiguous amino acids, more preferably about 80. An amino acid sequence from the second reading frame may be preferred. A stop codon occurs in this frame at nucleotide 251, so in a preferred embodiment the polypeptide includes a contiguous sequence of amino acids encoded by the nucleotide sequence of the second reading frame of FIG. 8 up to said stop codon. Usually, additional amino acids are included N-terminal to the amino acid sequence shown.

On the other hand, the encoded polypeptide may include an amino acid sequence which differs by one or more amino acid residues from the relevant amino acid sequence shown in FIG. 8. Nucleic acid encoding a polypeptide which is an mino acid sequence mutant, variant, derivative or allele of sequence shown in FIG. 8 is further provided by the resent invention.

Nucleic acid encoding such a polypeptide may show at the nucleotide sequence and/or encoded amino acid level greater than about 50% homology with the relevant coding/amino acid sequence shown in FIG. 8, greater than about 60% homology, greater than about 70% homology, greater than about 80% homology, greater than about 90% homology or greater than about 95% homology.

As is well-understood, homology at the amino acid level is generally in terms of amino acid similarity or identity. Similarity allows for "conservative variation", such as substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the relevant amino acid sequence of FIG. 6, or may more preferably be over a contiguous sequence of about 20, 25, 30, 40, 50, 60, 70, 80 or more amino acids, compared with the relevant amino acid sequence of FIG. 8.

At the nucleic acid level, homology may be over the full-length or more preferably by comparison with the a contiguous nucleotide coding sequence within the sequence of FIG. 8 of about 50, 60, 70, 80, 90, 100, 120, 150, 180, 210, 240 or more nucleotides.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. where nucleic acid according to the invention includes RNA, reference to the sequence shown should be construed as Inference to the RNA equivalent, with U substituted for T.

Nucleic acid sequences encoding all or part of the gene and/or its regulatory elements can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992).

The sequence information provided in FIG. 8 enables cloning of the full-length human coding sequence. The present invention provides a method of obtaining nucleic acid of interest, the method including hybridisation of a probe having the sequence shown in FIG. 8 or a complementary sequence, or a suitable fragment of either, to target nucleic acid. Hybridisation is generally followed by identification of successful hybridization and isolation of nucleic acid which has hybridised to the probe, which may involve one or more steps of PCR. The nucleic acid sequences provided herein readily allow the skilled person to design PCR primers for amplification of the full-length sequence.

Nucleic acid according to the present invention is obtainable using one or more oligonucleotide probes or primers designed to hybridise with one or more fragments of the nucleic acid sequence shown in FIG. 8 particularly fragments of relatively rare sequence, based on codon usage or statistical analysis. A primer designed to hybridise with a fragment of the nucleic acid sequence shown in FIG. 8 may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with the sequence shown in FIG. 8 and a primer which hybridises to the oligonucleotide linker.

Such oligonucleotide probes or primers, as well as the full-length sequence (and mutants, alleles, variants and derivatives) are also useful in screening a test sample containing nucleic acid for the presence of alleles, mutants and variants, with diagnostic and/or prognostic implications.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR), as discussed.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

Those skilled in the art are well able to employ suitable conditions of the desired stringency for selective hybridisation, taking into account factors such as oligonucleotide length and base composition, temperature and so on.

On the basis of amino acid sequence information, oligonucleotide probes or primers may be designed, taking into account the degeneracy of the genetic code, and, where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18–20. Those skilled in the art are well versed in the design of primers for use processes such as PCR. Various techniques for synthesizing oligonucleotide primers are well known in the art, including phosphotriester and phosphodiester synthesis methods.

A further aspect of the present invention provides an oligonucleotide or polynucleotide fragment of the nucleotide sequence shown in FIG. 8, or a complementary sequence, in particular for use in a method of obtaining and/or screening nucleic acid. Some preferred oligonucleotides have a sequence shown in FIG. 8 or a sequence which differs from any of the sequences shown by addition, substitution, insertion or deletion of one or more nucleotides, but preferably without abolition of ability to hybridise selectively with nucleic acid with the sequence shown in FIG. 8, that is wherein the degree of homology of the oligonucleotide or polynucleotide with one of the sequences given is sufficiently high.

Nucleic acid according to the present invention may be used in methods of gene therapy, for instance in treatment of individuals with the aim of preventing or curing (wholly or partially) a disease. This may ease one or more symptoms of the disease.

A convenient way of producing a polypeptide according to the present invention is to express nucleic acid encoding it, by use of the nucleic acid in an expression system.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Nucleic acid may be introduced into a host cell and this may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

The skilled person can use the techniques described herein and others well known in the art (for which see e.g. the Sambrook and Ausubel references cited herein) to produce large amounts of polypeptide, or fragments or active portions thereof, for use as pharmaceuticals, in the developments of drugs and for further study into its properties and role in vivo.

Thus, a further aspect of the present invention provides a polypeptide which includes an amino acid sequence shown in FIG. 8 as discussed, which may be in isolated and/or purified form, free or substantially free of material with which it is naturally associated, such as other polypeptides or such as human polypeptides other than polypeptide or (for example if produced by expression in a prokaryotic cell) lacking in native glycosylation, e.g. unglycosylated.

Polypeptides which are amino acid-sequence variants, alleles, derivatives or mutants are also provided by the present invention, as has been discussed. Preferred such polypeptides have function, that is to say have one or more of the following properties: immunological cross-reactivity with an antibody reactive with a polypeptide for which the sequence is given in FIG. 8; sharing an epitope with a polypeptide for which the amino acid sequence is shown in FIG. 8 (as determined for example by immunological cross-reactivity between the two polypeptides.

The present invention also includes active portions, fragments, derivatives and functional mimetics of the polypeptides of the invention. A fragment of the polypeptide may be a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptide sequence antigenic determinants or epitopes useful for raising antibodies to a portion of the amino acid sequence.

A polypeptide, peptide fragment, allele, mutant or variant according to the present invention may be used in phage display or other technique (e.g. involving immunisation) in obtaining specific antibodies. Antibodies are useful in purification and other manipulation of polypeptides and peptides, diagnostic screening and therapeutic contexts.

The provision of the novel polypeptides enables for the first time the production of antibodies able to bind it specifically, and by procedures other than the signal transfer selection which led to its identification and the isolation of antibody CD4E1 as described in Example 16. Accordingly, a further aspect of the present invention provides an antibody able to bind specifically to a polypeptide including a sequence given in FIG. 8.

Such antibodies may be obtained by selection on peptides or proteins including amino acid sequences of FIG. 8, e.g. using phage display libraries as in WO92/01047, or by using such peptides or proteins to immunise animals and obtain monoclonal antibodies or polyclonal antisera.

Antibodies identified, erg. by phage display, may then be used to identify further proteins, e.g. receptor molecules, which may be complexed with the protein including the amino acid sequence of FIG. 8, using techniques of signal transfer selection as disclosed herein.

cDNA expression libraries, for example displayed on phage, may be used in conjunction with signal transfer selection to identify ligands which bind molecules, such as receptors, in the vicinity of protein including the amino acid sequence of FIG. 8. An antibody, e.g. with a myc tag, may bind to the protein on the surface of CD4 lymphocytes. the phage-displayed cDNA expression library may be added, followed by the antibody 9E10 (which binds to the myc tag) conjugated to HRP. Adition of biotin-tyramine would then lead to the labelling of molecules in the vicinity of the antibody, including phage expressing receptor ligands. The antibody CD4E1 would be suitable for this.

The polypeptides, antibodies, peptides and nucleic acid of the invention may be formulated in a composition. Such a composition may include, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

A polypeptide according to the present invention may be used in screening for molecules which affect or modulate its activity or function, including ability to interact or associate with another molecule, such as CC-CKR5 or other molecule, e.g. on the surface of CD4+ cells. Such molecules may be useful in a therapeutic (possibly including prophylactic) context.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide or protein libraries may be preferred.

As an alternative to using signal transfer selection to identify molecules which interact with protein including an amino acid sequence shown in FIG. 8, test substances may be screened for ability to interact with the polypeptide, e.g. in a two-hybrid system (which requires that both the polypeptide and the test substance can be expressed, e.g. in a cell such as a yeast or mammalian cell, from encoding nucleic acid). This may be used as a coarse screen prior to testing a substance for actual ability to modulate activity of the polypeptide. The screen may be used to screen test substances for binding to a specific binding partner, to find mimetics of polypeptide, e.g. for testing as anti-tumour therapeutics. Two-hybrid screens may be used to identify a substance able to modulate, e.g interfere with, interaction between two polypeptides or peptides.

The two-hybrid screen assay format is described by Fields and Song, 1989, Nature 340; 245–246. This type of assay format can be used in both mammalian cells and in yeast. various combinations of DNA binding domain and transcriptional activation domain are available in the art, such as the LexA DNA binding domain and the VP60 transcriptional activation domain, and the GAL4 DNA binding domain and the GAL4 transcriptional activation domain. Suitable fusion constructs are produced for expression within the assay system. When screening for a susbstance able to modulate an interaction between two components, test substances (e.g. in a combinatorial peptide library) may be expressed from a third construct.

Following identification of a substance which modulates or affects polypeptide activity and/or its ability to interact with or associate with another molecule, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of cancer, use of such a substance in manufacture of a composition for administration, e.g. for treatment of cancer, and a method of making a pharmaceutical composition comprising admixing such a substance with a pharmaceutically acceptable excipient, vehicle or carrier, and optionally other ingredients.

Further aspects of the invention and embodiments will be apparent to those skilled in the art. All documents mentioned herein are incorporated by reference. In order that the present invention may be fully understood the following examples are provided by way of exemplification only and not by way of limitation.

BRIEF DESCRIPTION OF THE DRAWINGS

FIG. 3(a) illustrates a process in which HRP-marker ligand conjugate directs the signal transfer of biotin tyramine (BT) onto phage binding around the ligand. Biotinylated phage are then allowed to bind cells in the absence of ligand, as shown in FIG. 3(b).

FIG. 3(b) shows binding of biotinylated phage in the absence of the original marker ligand. Streptavidin-HRP is added and a new aliquot of phage library then added (illustrated in black) which can then be biotinylated by signal transfer and selected. In the illustrated embodiment, the selected phage mimics the ligand and inhibits its binding to cells.

FIG. 6(a) shows results with mononuclear cells from blood labelled with anti-CD36.

FIG. 6(b) shows results for control enrichment, no CD36 antibody added at the start.

FIG. 6(c) shows results for enriched cells labelled with anti-CD36.

Figure 8:
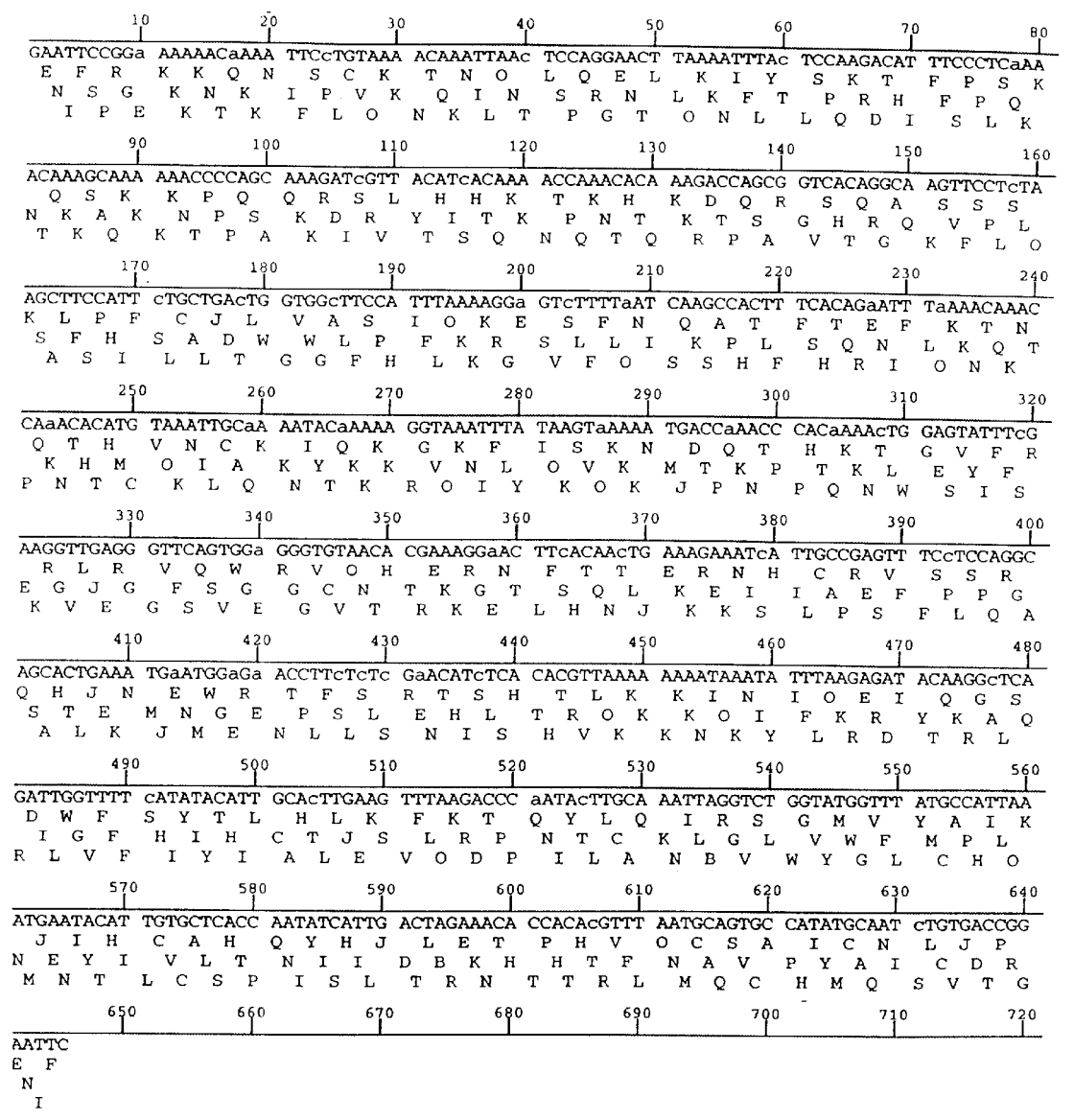

FIG. 8 shows nucleotide and amino acid sequences for the human homologue of the rat gene CL-6 identified for the first time in the work described in Example 16. EcoRI cloning sites are underlined.

For one specific embodiment of the present invention, the procedure may be summarised as follows, for purposes of illustration.

The exemplary system is based upon the use of immobilised reporter enzyme to catalyse the deposition of multiple copies of biotinylated tyramine molecules around the site of enzyme activity. Catalysed enzyme reporter deposition (CARD) has been used as a means of signal amplification in immunocytochemistry, ELISA and blotting formats (Bobrow et al. (1992) J. Immunol. Methods, 125: 279–285). The invention here comes from the realisation that the deposition of a reporter molecule can be used not only as an amplification system, but also as a transfer system which allows recovery of tagged ligands.

Figure 1:
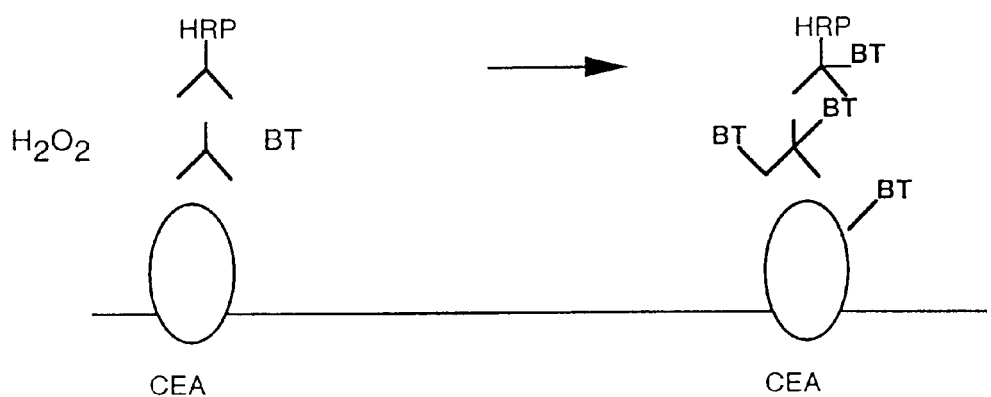
FIG. 1 shows a schematic representation of a process according to one embodiment of the present invention. A target antibody able to bind the antigen of interest (CEA) is labelled by biotinylation because it binds the antigen in the region of binding of a marker ligand which comprises a monoclonal antibody specific for CEA joined to the enzyme hydrogen peroxidase. In the presence of hydrogen peroxide, the hydrogen peroxidase catalyses binding of biotin-tyramine to molecules in the vicinity of the enzyme, including the target antibody. (CEA—carcinoembronic antigen; HRP—horseradish peroxidase, a hydrogen peroxidase; BT—Biotin-tyramine.)

In the example described here, horseradish peroxidase (HRP) activity is used to catalyse biotinylated tyramine molecule deposition. HRP activity is targeted to a specific site of interest, e.g. on a cell surface, by the use of a primary mouse Mab with a desired binding specificity, the HRP activity being provided by an anti-mouse-HRP conjugated second antibody which recognises the primary Mab. HRP activity may alternatively be provided by direct conjugation of the Mab or ligand to the enzyme (e.g. by expression as a fusion protein). Phage particles displaying antibody antigen binding domains are incubated on the cell surface along with the primary Mab, and those binding around the site of the primary Mab, and hence around the site of HRP activity, become covalently linked to biotin tyramine molecules. This reaction is catalysed by oxygen free radicals generated by the HRP in the presence of $H_2O_2$ (FIG. 1).

Biotinylated phage may then be specifically recovered using streptavidin coated magnetic beads and hence phage which bind in close proximity to the existing mouse Mab are enriched for. The half life of the biotin-tyramine phenolic free radical is very short, so deposition occurs extremely close to the activating enzyme (Bobrow et al., supra). When CARD is used as an amplification system to enhance signal in immunocytochemistry no detectable loss of image resolution is apparent, indicating that deposition occurs in close association with the catalytic enzyme (Adams, J. C.(1992) J. Histochem. and Cytol. 40: 1457–1463). The area over which the signal transfer occurs may be increased or decreased by modifying the viscosity or temperature of the solution in which the reaction is carried out, or by adding excess unbiotinylated tyramine.

Signal transfer selection has general applications to the identification of protein-protein interactions and in some ways is analogous to the yeast two-hybrid system which has proved to be a very powerful technique for the detection of such interactions (Fields and Song, 1989, Nature 340, 245–246). Both systems involve a tagged known protein which can be paired with a library of unknown proteins, some of which may interact with the tagged protein. Interaction between the two proteins in the two hybrid system results in transcriptional activation of the yeast GAL1-lacZ gene which encodes enzymes for galactose utilisation and hence allows selection of the interacting clone on galactose-containing media. Interaction of the two proteins in the signal transfer system results in labelling of the unknown protein, e.g. phage-displayed antibody, peptide or other protein and hence recovery of that moiety. If phage-displayed antibody, peptide or other protein is the labelled (e.g biotinylated) element then rescue of the gene for the interacting protein is facilitated, since in phage display each phage particle contains nucleic acid encoding the antibody, peptide or other protein it displays (see e.g. WO92/01047). Signal transfer selection is not confined to intracellular expression in yeast, and as such has many advantages over the yeast two-hybrid system.

Examples 15 and 16 demosntrate how signal transfer selection may be used as a tool for discovering novel protein-protein interactions. Examples of the types of protein-protein interactions which may be identified include proteins interacting in signal transduction pathways, such as G proteins, kinases, phosphatases. Receptors often exist as multiprotein complexes, interacting pairs of which may be identified either in the presence or absence of ligand binding. Protein-protein interactions which occur within the cell may also be identified, for instance using cell extracts, inside-out vesicles, nuclear extracts and extracts from other cellular compartments, either in solution or immobilised on a solid support. The present invention may also be applied to the identification of protein-DNA interactions. Segments of DNA encorporating putative transcription factor binding domains may be labelled (e.g. biotinylated) and coupled to enzyme-associated binding molecule for the label (e.g. streptavidin). Proteins which bind the DNA sequence may be selected by signal transfer selection.

There are many applications of signal transfer selections, which will be evident to people skilled in the art. Applications include the isolation of antibodies which specifically recognise a ligand-receptor complex, using an enzyme conjugate ligand to target the selection of such antibodies. Specific labelling of one cell type over and above background cell types may be achieved. For example, cells expressing one particular surface antigen may be labelled using an enzyme-conjugated sbp member which recognises that antigen and which can transfer label to those cells alone. This allows purification of the antigen-expressing cell type from a background of cells which do not express the antigen and do not, therefore, become labelled (or not significantly so). This is exemplified in Example 20.

Signal transfer labelling need not be limited to cell surfaces. Any protein, virus particle or other species in a complex mix may be labelled specifically and purified away from the unlabelled population.

Signal transfer has applications to signal enhancement in flow cytometry, as discussed and demonstrated in Examples 18 and 19. The signal enhancement profile may be used for particular molecules, e.g. on a cell surface, to assess copy number of that molecule, e.g. on a particular cell or cell type, or to asess the proximity of two or more different target molecules, e.g. on the same cell, as well as providing a more sensitive method for detection of a particular protein, e.g. on a cell surface.

Another application is that of reverse drug screening. In this process a drug which is known to be efficacious, but the cellular target of which is unknown, may be conjugated to the enzyme which directs label deposition. The drug-enzyme complex may then be incubated with cellular extracts and the labelling molecule added. Proteins in the cellular extract which bind to the drug-enzyme conjugate then become labelled, allowing for their purification and characterisation.

Since the signal transfer selection mechanism relies on the generation of free radicals use may be made of the generation of free radicals by a protein or putative enzyme to select for a protein with novel or enhanced catalytic activity. Phage libraries of proteins, enzymes, or putative catalytic antibodies may be made and selection may be directed by the labelling (e.g. biotinylation) of active species due to their ability to generate free radicals which activate the label (e.g. biotin tyramine) and cause its deposition on the phage displayed species.

Signal transfer technology also has a number of in vivo applications, for example in tumour targeting. An antibody-HRP conjugate which specifically recognises a tumour type may be allowed to localise to the tumour in vivo. Biotin tyramine, or a similar molecule, may then be injected, and the HRP may catalyse biotin tyramine deposition specifically at the tumour site. This would result in a heavily biotinylated tumour to which streptavidin-conjuagte drugs, or streptavidin-liposomes as vechicles for gene therapy or drug delivery, may be targeted.

Signal transfer is a process which can be re-iterated resulting in the successive build up of biotin tyramine molecules around a focus of enzyme activity. This may have in vivo applications e.g. in the context of arteriole or nerve repair since successive layers of biotin tyramine, or similar molecules, may be depositied at sites of damage to generate complexes which may block damaged vessels.

The iterative potential of biotin-tyramine and other label desposition in accordance with the present invention may be used in the generation of oriented surfaces. Successive layers of proteins, or other species, may be deposited on the surface. An initial protein, or other species, may be immobilised on a surface and a binding molecule specific for this initial protein may be enzyme—(e.g. HRP-) conjugated and allowed to bind to the surface, then used to deposit a layer of biotine tyramine over the initial surface. A second, e.g., streptavidin-linked protein, or other species, may then be added to the surface, giving a layer of the second protein. This process may be re-iterated as required to build up complex oriented layers on surfaces.

A model system has been used to exemplify the potential of this invention utilising a HeLa cell line which has been transfected with the gene for human carcinoembryonic antigen (CEA). A scFv which specifically recognises CEA has been used for initial experiments and a large scFv phage display library has been used to generate further anti-CEA specific scFv's using the signal transfer selection system.

Further experiments have been carried out to select for specific cell surface proteins on cultured human endothelial cells.

LIST OF EXAMPLES

EXAMPLE 1—Recovery of CEA-binding phage from the surface of cells expressing CEA in the presence or absence of a marker anti-CEA mouse antibody.

EXAMPLE 2—Selection of human CEA-binding phage from a large library of human scFv's.

EXAMPLE 3—$K_{off}$ determination for scFv fragments binding to CEA.

EXAMPLE 4—Selection of phage which bind to the mouse anti-CEA antibody from a large library of human scFv's.

EXAMPLE 5—Marker-ligand-dependent biotinylation of a CEA-expressing cell type.

EXAMPLE 6—Marker-ligand dependent biotinylation of CEA.

EXAMPLE 7—Selection of human E-selectin-binding phage from a large library of human scFv's.

EXAMPLE 8—Selection of novel anti-TGFβ1-binding phage using an existing anti-TGFβ1-specific scFv.

EXAMPLE 9—Selection of anti-chemokine receptor phage using a chemokine ligand to guide selection.

EXAMPLE 10—Selection of anti-chemokine receptor phage using-light-activated streptavidin and the receptor ligand to guide.

EXAMPLE 11—Selection of phage antibodies to two different cell surface adhesion molecules using a biotinylated ligand which binds to both to guide selection.

EXAMPLE 12—Measurement of the distance over which signal transfer using biotin tyramine may occur.

EXAMPLE 13—Step-back selection to isolate phage antibodies which inhibit ligand binding.

EXAMPLE 14—Biotin tyramine selection in solution using a peptide phage library.

EXAMPLE 15—Characterisation of clones which bind to CD4+ cells, but not to the chemokine receptor CC-CXR5, by Western blotting and ICC.

EXAMPLE 16—Demonstration of the use of signal transfer selection to identify novel protein-protein interactions.

EXAMPLE 17—Biotinylation of CD4E1 phage on the cell surface using MIP-1α to direct the biotinylation.

EXAMPLE 18—Use of biotin tyramine as a signal amplification reagent in flow cytometry.

EXAMPLE 19—Iteration of biotin tyramine treatment to give further signal enhancement.

EXAMPLE 20—Use of biotin tyramine to specifically biotinylate subpopulations of cells to allow their subsequent purification.

EXAMPLE 21—Biotinylation of phage particles in solution to validate biotin-tyramine preparations.

EXAMPLE 1

Recovery of CEA-binding Phage from the Surface of Cells Expressing CEA in the Presence of a Marker Anti-CEA Mouse Mab a. Purification of CEA-binding phage CEA6 is a CEA specific scFv isolated from a large scFv phage display library by panning on human CEA (Vaughan et al 1996). OP1 is a control scFv which recognises a 16 residue. peptide and does not bind to CEA. Phagemid particles expressing CEA6 or OP1 scFv's as a fusion proteins with the phage gIII protein were isolated as follows. 500 ml prewarmed (37° C.) 2YTAG (2TY media supplemented with 100 μg/ml ampicillin and 2% glucose) in a 2 l conical flask was inoculated with approximately $3 \times 10^{10}$ cells from a glycerol stock (−70° C.) of CEA6- or OP1-phagemid. The culture was grown at 37° C. with good aeration until the OD 600 nm reached 0.8. M13K07 helper phage (Stratagene) was added to the culture to a multiplicity of infection (moi) of approximately 10 (assuming that an OD 600 nm of 1 is equivalent to $5 \times 10^8$ cells per ml of culture The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2TYAK (2YT media supplemented with 100 μg/ml ampicillin and 50 mg/ml kanamycin), and the culture incubated overnight at 30° C. with good aeration (300rpm) Phage particles were purified and concentrated by three polyethylene glycol (PEG) precipitations (Sambrook, J., Fritsch, E. F., and Maniatis, T. (1990). Molecular Cloning—A Laboratory Manual. Cold Spring Harbour, New York) and resuspended in PBS to $10^{12}$ transducing units (tu)/ml.

b. Preparation of HeLa-CEA cell slides.

CEA-expressing HeLa cells were grown to confluence in DMEM supplemented with 10% fetal calf serum on 16 chamber slides (Nunc). The cells were fixed with acetone for 10 minutes, dried and stored at −70° C.

c. Biotinylation of tyramine.

An equimolar amount of tyramine (sigma) was allowed to react with NHS-LC-biotin in 50 mM borate buffer, pH 8.8. The reaction was carried out at room temperature overnight in the dark with rotation. The biotinylated tyramine (BT) was filtered through a 0.45 μM filter, aliquotted and stored at −70° C.

d. Biotinylation of phage binding in close proximity to the Mab.

HeLa-CEA slides were incubated overnight at 4° C. with 100 μl phage in the presence or absence of an anti-CEA mouse Mab (Zymed) at a range of dilutions from 1:100 to 1:10000 in 3% marvel PBS (MPBS). Phage imput values were around $5 \times 10^{11}$ per ml for CEA-purified phage. Control incubations were carried out in parallel using a phage preparation of OP1 in the presence of the anti-CEA Mab. 100 μl of phage were used per chamber of the slide. Slide chambers were washed 3 times in PBS containing 0.1% Tween 20 (PBST), followed by 3 washes with PBS. Each wash was left for 2 minutes before being changed. 100 μl of a goat anti-mouse HRP second antibody (Pierce) was then added at a dilution in MPBS of 1:2500 and incubated for 1 hour at room temperature. Control incubations were carried out for the same length of time incubating with PBS alone. Washing was carried out as before and 100 μl of BT in 50 mM Tris-HCl pH 7.4 with 0*03% $H_2O_2$ was added to each slide chamber for 10 minutes at room temperature. Control incubations were carried out as above, but with the omission of the BT. Chambers were washed as above and phage were then eluted using 200 μl triethylamine (TEA). TEA was neutralised with 100 μl of 1M Tris-HCl pH 7.4. 10 μl of this eluted phage was used to directly infect an exponentially growing culture of E coli TG1. Infected cells were grown for 1 hour at 37° C. with light aeration in 2YT broth, and then plated on 2TYAG medium. A series of dilutions of bacteria were plated out and incubated at 30° C. overnight. Colony counts gave the phage titre. The results are shown in Table 1.

e. Capture of biotinylated phage on streptavidin-coated magnetic beads.

20 μl of streptavidin-coated magnetic beads (Dynal) were taken out of solution using a magnet and blocked for 2 hours at room temperature on a rotating platform with 1 ml of 3% MPBS. Beads were pelleted using a magnet and 150 μl of eluted phage with 30 μl of 15% MPBS were then added to the blocked beads and rotated for 15 minutes at room temperature.

Beads were pelleted, washed 3 times in PBST and 3 times in PBS. The beads were resuspended in a final volume of 100 μl PBS. Half of this was taken and used to directly infect 1 ml of an exponentially growing culture of E coli TG1. Infected cells were grown for 1 hour at 37° C. with light aeration in 2YT broth, and then plated on 2TYAG medium.

A series of dilutions of bacteria were plated out and incubated at 30° C. overnight. Colony counts gave the phage titre. The results are shown in Table 1.

2. Summary of the results—enhanced recovery of CEA-binding phage using signal transfer selection followed by streptavidin capture.

Incubations of CEA6 purified phage on slides coated with CEA transfected HeLa cells were carried out under a range of different conditions. Phage imput, primary Mab dilution, presence or absence of HRP-conjugated second antibody and presence or absence of BT were all examined. OP1, a non-CEA-specific phagemid which had been selected on a 16 residue peptide was also included. The data are shown in Table 1.

CEA6 phage incubated in the presence of primary Mab, anti-mouse-HRP conjugated second antibody and ST consistently gave the highest number of phage recovered on the streptavidin-coated magnetic beads. When BT was omitted the number of phage recovered fell by 16-fold, and when the primary Mab was omitted phage recovery was reduced by 8-fold. Absence of the HRP conjugated Mab resulted in a 6-fold reduction in phage recovery supporting the conclusion that biotinylation of CEA6 phage is driven by the presence of the Mab-HRP complex. This also demonstrates that only a small proportion of phage are binding non-specifically to the Dynal beads in the absence of BT. Some non-site-specific biotinylation of phage must be occurring since the recovery of phage in the presence of BT, but absence of primary Mab is greater than the recovery when BT is omitted. Absence of the HRP-antibody conjugate has a simlar effect on the number of phage recovered compared with absence of the primary Mab. This suggests that the secondary Mab is binding specifically to the primary Mab and gives little background binding to the cells themselves. The non-CEA-specific phage gave similar levels of biotin-phage recovery as those seen in the absence of the primary anti-CEA Mab, again suggesting a low level of non-site-specific phage biotinylation.

Overall the results provide an exemplary demonstration of how an existing Mab raised to a protein of interest can be used to guide catalysis of biotin deposition onto phage binding the protein of interest in the same vicinity as that Mab.

EXAMPLE 2

Selection of CEA-binding Phage from a Large Library of Human scFv's

Antibody repertoire

The following antibody repertoire was used: Large single chain Fv library derived from lymphoid tissues including tonsil, bone marrow and peripheral blood lymphocytes.

Polyadenylated RNA was prepared from the B-cells of various lymphoid tissues of 43 non-immunised donors using the "Quickprep mRNA Kit" (Pharmacia). First-strand cDNA was synthesized from mRNA using a "First-strand cDNA synthesis" kit (Pharmacia) using random hexamers to prime synthesis. V-genes were amplified using family-specific primers for VH, Vκ and Vλ genes as previously-described (Marks et al., (1991) J. Mol. Biol. 222:581–597) and subsequently recombined together with the $(Gly_4, Ser)_3$ scFv linker by PCR assembly. The VH-linker-VL antibody constructs were cloned into the Sfi I and Not I sites of the phagemid vector, pCANTAB 6. Ligation, electroporation and plating out of the cells was as described previously (Marks et al, supra). The library wan made ca. 1000× larger than that described previously by bulking up the amounts of vector and insert used and by performing multiple electroporations. This generated a scFv repertoire that was calculated to have ca. $1.3 \times 10^{10}$ individual recombinants which by Bst NI fingerprinting were shown to be extremely diverse.

a. Induction of phage antibody library

The phage antibody repertoire above was selected for antibodies to CEA. The 'large' scFv repertoire was treated as follows in order to rescue phagemid particles. 500 ml prewarmed (37° C.) 2YTAG (2YT media supplemented with 100 μg/ml ampicillin and 2% glucose) in a 2 l conical flask was inoculated with approximately $3 \times 10^{10}$ cells from a glycerol stock (−70° C.) culture of the library. The culture was grown at 37° C. with good aeration until the OD600 nm reached 0.7 (approximately 2 hours). M13K07 helper phage (Stratagene) was added to the culture to a multiplicity of infection (moi) of approximately 10 (assuming that an OD600 nm of 1 is equivalent to $5 \times 10^8$ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2YTAK (2YT media supplemented with 100 μg/ml ampicillin and 50 μg/ml kanamycin), and the culture incubated overnight at 30° C. with good aeration (300 rpm). Phage particles were purified and concentrated by three polyethylene glycol (PEG) precipitations (Sambrook, J., Fritsch, E. F., & Maniatis, T. (1990). Molecular Cloning—A Laboratory Manual. Cold Spring Harbour, New York) and resuspended in PBS to $10^{12}$ transducing units (tu)/ml (ampicillin resistant clones).

b. Selection of CEA-binding phage from a large non-immunised phase display library using catalysed enzyme reporter deposition followed by streptavidin capture.

i. First round of selection

Two rounds of selection using phage prepared from a large non-immunised human scFv library were carried out on slides of CEA-expressing HeLa cells. $5 \times 10^{11}$ phage were allowed to bind to the cells in the presence or absence of an anti-CEA mouse Mab (Zymed) at a dilution of 1:100 in MPBS in a total volume of 100 μl, at 4° C. overnight. Slides were washed three times in PBST followed by three times in PBS. A secondary anti-mouse hydrogen-peroxidase-conjugated antibody which recognised the primary mouse anti-CEA antibody was then incubated on the sections at a dilution of 1:2500 in MPBS in a total volume of 100 μl at room temperature for 1 hour. gashing was carried out as before and 100 μl of biotinylated-tyramine in 50 mM Tris-HCl pH 7.4 with 0.03% $H_2O_2$ was added to each slide chamber for 10 minutes at room temperature. Chambers were washed as above and phage were eluted using 200 μl triethylamine (TEA). TEA was neutralised with 100 μl of 1M Tris-HCl pH 7.4.

ii. Assessment of the total number of phage binding to the HeLa-CEA cells 10 ml of this eluted phage was used to directly infect an exponentially growing culture of E coli TG1 with light aeration in 2TY broth at 37° C. for 1 hour. Infected TG1s were plated on 2TYAG medium in 243 mm×243 mm dishes (Nunc). Dilutions of infected TG1s were also plated out and incubated at 30° C. overnight. Colony counts gave the phage output titre.

iii. Recovery of biotinylated phage on streptavidin-coated magnetic beads

20 μl of streptavidin-coated magnetic beads (Dynal) were taken out of solution using a magnet and blocked for 2 hours at room temperature on a rotating platform with 1 ml of 3VMPBS. Beads were pelleted and 150 μl of eluted phage with 30 μl of 15% MPBS were then added to the blocked beads and rotated for 15 minutes at room temperature. Beads were pelleted, washed 3 times in 1 ml PBST and 3 times in 1 ml PBS. The beads were resuspended in a final volume of 100 μl PBS. 50 μl of this was taken and used to directly infect 1 ml of an exponentially growing culture of E. coli TG1 at 37° C. for 1 hour with light aeration in 2TYAG medium. Infected TG1s were plated on 2TYAG medium in 243 mm×243 mm dishes (Nunc). Dilutions of bacteria were also plated out and incubated at 30° C. overnight. Colony counts gave the phage output titre.

iv. Second round of selection

Colonies were scraped off the 243 mm×243 mm plates into 3 ml of 2TY broth and 15% (v/v) glycerol added for storage at −70° C. Glycerol stock solutions from the first round of selection of the repertoire on the HeLa-CEA cells were rescued using helper phage to derive phagemid particles for the second round of selection. Phagemid particles were rescued from both first round selections carried out in the presence or in the absence of the marker anti-CEA Mab 250 μl of glycerol stock was used to inoculate 50 ml 2YTAG broth, and incubated in a 250 mL conical flask at 37° C. with good aeration until the OD600 nM reached 0.7 (approximately 2 hours). M13K07 helper phage (moi=10) was added to the culture which was then incubated stationary at 37° C. for 15 minutes followed by 45 minutes with light aeration (200 rpm) at the same temperature. The culture was centrifuged and the supernatant-drained from the cell pellet. The cells were resuspended in 50 ml prewarmed 2YTAK, and the culture incubated overnight at 30° C. with good aeration. Phage particles were purified and concentrated by PEG precipitation (Sambrook et al., 1990) and resuspended in PBS to $10^{13}$ tu/ml.

Phage recovered from the selection in the presence of the anti-CEA mouse Mab underwent a second round selection with either no Mab, or with a 1:100, or a 1:1000 dilution of the anti-CEA Mab. Phage recovered from the first round of selection in the absence of the anti-CEA Mab underwent a second round of selection, again in the absence of the anti-CEA Mab. The selections were carried out on the HeLa-CEA cells as described for the first round of selection. The total numbers of phage present in the eluates and recovered by streptavidin capture are shown in Table 2.

The total number of phage recovered on the magnetic beads after the first round of selection was comparable either in the presence or absence of Mab. At round two of the selection the total number of recovered phage had dropped to around one tenth of the value from round one. It was, however, notable that the number of phage recovered after two rounds of selection in the presence of Mab was around 7-fold higher than that recovered after two rounds of selection without the Mab being present. When one round with Mab present was followed by one round without the Mab the number of recovered phage was around half of that seen after two rounds of selection with the Mab. Ten-fold dilution of the Mab at round 2 of the selections slightly reduced the number of phage recovered on the Dynal beads (by 12%).

c. Growth of single selected clones for immunoassay

Individual colonies from the first and second round selections were used to inoculate 100 μl 2YTAG into individual wells of 96 well tissue culture plates (Corning). Plates were incubated at 30° C. overnight with moderate shaking (200 rpm). Glycerol to 15% was added to each well and these master plates stored at −70° C. until ready for analysis.

d. Soluble ELISA to identify anti-CEA scFv

Cells from the master plates were used to inoculate fresh 96 well tissue culture plates containing 100 μl 2YTAG per well. These plates were incubated at 30° C. for 8 hours then centrifuged at 2000 rpm for 10 min and the supernatant eluted. Each cell pellet was resuspended in 100 μl 2YTA containing 10 mM IPTG and incubated at 30° C. overnight.

Each plate was centrifuged at 2000 rpm and the 100 μl supernatant from each well recovered and blocked in 20 μl 18% M6PBS stationary at room temperature for 1 hour. Meanwhile, flexible microtitre plates which had been blocked overnight stationary at 37° C. with either 100 μl 0.5 μg/ml CEA in dH₂O or 100 μl dH₂O alone, were washed 3 times in PBS and blocked for 2 h stationary at room temperature in 3MPBS. These plates were then washed three times with PBS and 50 μl preblocked soluble scFv added to each well of both the CEA-coated or uncoated plate. The plates were incubated stationary at 37° C. for 1 h after which the scFv solutions were poured off. The plates were washed by incubating for 2 min in PBST three times followed by incubating for 2 min in PBS three times, all at room temperature.

To each well of both the CEA-coated and the uncoated plate, 100 μl of a 1 in 200 dilution of the anti-myc tag murine antibody 9E10 (Munro, S. & Pelham, H. R. E. (1986) Cell 46, 291–300) in 3MPBS was added and the plates incubated at 37° C. stationary for 1 h. Each plate was washed as described above and 100 μl of a 1 in 5000 dilution goat anti-mouse alkaline phosphatase conjugate (Pierce) in 3MPBS added and incubated stationary at 3° C. for 1 h. Plates were washed as described above followed by two rinses in 0.9% NaCl. Alkaline phosphatase activity was visualised using the chromagenic substrate pNPP (Sigma). The absorbance signal generated by each clone was assessed by measuring the optical density at 405 nm (pNPP) using a microtitre plate reader. Clones were chosen for further analysis if the ELISA signal generated on the CEA-coated plate was at least double that on the uncoated plate. The number of clones screened from each round of selection and the number of CEA positives are shown in Table 3.

e. Sequencing of anti-CEA ScFv Antibodies

The nucleotide sequences of the anti-CEA antibodies were determined by first using vector-specific primers to amplify the inserted DNA from each clone. Cells from an individual colony on a 2YTAG agar plate were used as the template for a polymerase chain reaction (PCR) amplification of the inserted DNA using the primers pUC19 reverse and fdtetseq. Amplification conditions consisted of 30 cycles of 94° C. for 1 min, 55° C. for 1 min and 72° C. for 2 min, followed by 10 min at 72° C. The PCR products were purified using a PCR Clean-up Kit (Promega) in to a final volume of 50 μl H2O. Between 2 and 5 μl of each insert preparation was used as the template for sequencing using the Taq Dye-terminator cycle sequencing system (Applied Biosystems). The primers mycseq10 and PCR-L-Link were used to sequence the light chain of each clone and PCR-H-Link and pUC19reverse to sequence the heavy chain.

f. Sequence of the initial CEA-specific scFv antibodies

Twelve different CEA specific antibodies were isolated from the selections. Each clone name and its heavy and light chain germline is given below. The signal transfer method of selection is capable of generating a diverse panel of anti-CEA antibodies. None of these antibodies were isolated from experiments in which panning of the large scFv library was carried out directly on purified CEA, suggesting that signal transfer selection provides a way of accessing different antibody specificities from the library.

| CLONE | VH GERMLINE | VL GERMLINE |
|-------|-------------|-------------|
| SS1A4 | VH4 DP71 | VLambda2 DPL11 |
| SS1A11 | VH4 DP71 | VLambda2 DPL11 |
| SS1G12 | VH4 DP71 | VKappa1 L12a |
| SS22A4 | VH4 DP79 | VLambda1 DPL5/2 |
| SS22A8 | VH4 DP63 | VLambda3 DPL16 |
| SS22B7 | VH4 DP79 | VLambda1 DPL5/2 |
| SS22B1 | VH2 V11-5b | VLambda1 DPL2 |
| SS22D12 | VH3 V343 | VLambda1 DPL2 |
| SS22E4 | VH2 DP28 | Vkappa1 DPK8 |
| SS21B1 | VH4 DP70 | Vkappa1 DPK4 |
| SS21B7 | VH1 DP71 | Vlambda3 DPL16 |
| SSDS1 | VH4 DP78 | Vlambda3 DPL16 |

EXAMPLE 3

$K_{OFF}$ Determination for scFv Fragments Binding to Desialylated CEA a. $K_{off}$ determination by surface plasmon resonance The $K_{off}$'s for binding to CEA of the scFv fragments described in Example 2 were determined using desialylated CEA coupled to a CM5 sensor chip. 100 μg of CEA was resuspended in 0.1 M sodium acetate buffer pH 4.0 and desialylated using 1.375 mU sialidase (sigma). This was incubated for 4 hours at 37° C. with occasional shaking. The desialylated CEA was then oxidised using 1 unit of galactose oxidase per 500 μg of CEA in 10 mM phosphate buffer pH 7.0. This was incubated for 2 hours at 36° C. and desalted into 10 mM sodium acetate buffer pH 4.0. The CEA was then immobilised onto the sensor chip using the aldehyde group. 15 μl EDC/NHS coupling agent (Pierce) was passed over the chip at a flow rate of 5 μl/min. 35 μl of 5 mM hydrazine in water was then passed over the chip, followed by 35 μl of ethanolamine. 4 μl of 60 μg/ml treated CEA was passed over the chip at a flow rate of 2 μl/min followed by 40 μl of 0.1M sodium cyanoborohydride in 0.1M acetate buffer pH 4.0 at a flow rate of 5 μl/min. Approximately 1500 RU (resonance units) of CEA was bound using this method. 5000 RU and 800 RU CEA chips were made using this procedure.

$K_{off}$'s were calculated using the Bia-Evaluation software (Pharmacia). Saturation of the chip with purified scFv was demonstrated for each sample before $K_{off}$ was measured. Results are shown in table 4. The range of $K_{off}$'s of the selected antibodies suggests that recovery is dependent on the exact site of binding of the phage antibodies rather than the affinity of the interaction, as is the case with traditional selection methods. Signal transfer selection is, therefore, a route to obtaining a population of antibodies of diverse sequences and affinities which would not normally be obtained by other selection procedures.

EXAMPLE 4

Selection of Phage Which Bind to the Mouse Anti-CEA Antibody from a Large Library of Human scFv's The antibody repertoire used here and the method of phage induction was the same as that described in Example 2. The selections assayed were the same as those described in Example 2.

a. Growth of single selected clones for immunoassay Individual colonies from the first and second round. selections were used to inoculate 100 μl 2YTAG into individual wells-of 96 well tissue culture plates (Corning). Plates were incubated at 30° C. overnight with moderate shaking (200 rpm). Glycerol to 15% was added to each well and these master plates stored at −70° C. until ready for analysis.

b. Soluble ELISA to identify anti-scFv

Cells from the master plates were used to inoculate fresh 96 well tissue culture plates containing 100 μl 2YTAG per well. These plates were incubated at 30° C. for 8 hours then centrifuged at 2000 rpm for 10 min and the supernatant eluted. Each cell pellet was resuspended in 100 μl 2YTA containing 10 mM IPTG and incubated at 30° C. overnight.

Each plate was centrifuged at 2000 rpm and the 100 μl supernatant from each well recovered and blocked in 20 μl 18% M6PBS stationary at room temperature for 1 hour. Meanwhile, flexible microtitre plates which had been incubated overnight stationary at 37° C. with either 50 μl 0.1 μg/ml of anti-CEA mouse Mab in PBS or 50 μl PBS alone, were washed 3 times in PBS and blocked for 2 h stationary at room temperature in 3MPBS. These plates were then washed three times with PBS and 50 μl preblocked soluble scFv added to each well of both the anti-CEA-mouse Mab-coated or uncoated plate. The plates were incubated stationary at 37° C. for 1 h after which the scFv solutions were poured off. The plates were washed by incubating for 2 min in PBST three times followed by incubating for 2 min in PBS three times, all at room temperature.

To each well of both the mouse Mab-coated and the uncoated plate, 100 μl of a 1 in 200 dilution of biotinylated anti-myc tag murine antibody 9E10 (Munro, S. & Pelham, H. R. B. (1986) Cell 46, 291–300) in 3MPBS was added and the plates incubated at 37° C. stationary for 1 h. Each plate was washed as described above. Plates were then incubated with alkaline-phosphatase-streptavidin complex (DAKO) diluted 1:1000 in $dH_2O$. Plates were washed as described above followed by two rinses in 0.9% NaCl. Alkaline phosphatase activity was visualised using the chromogenic substrate pNPP (Sigma). The absorbance signal generated by each clone was assessed by measuring the optical density at 405 nm (pNPP) using a microtitre plate reader. Clones were scored for positive binders for the anti-CEA mouse Mab if the ELISA signal generated on the CEA-coated plate was at least double that on the uncoated plate.

Clones from the various round 2 selections were screened for anti-CEA mouse Mab binding (Table 5). 12.5% of clones which had come through two rounds of 1:100 Mab selections were found to bind the Mab. No Mab binders were present in the population which came through two rounds of selection with no Mab present. This demonstration that some of the recovered phage recognise the anti-CEA mouse Mab is evidence for general biotinylation of any phage binding in close proximity of the anti-mouse HRP secondary antibody and hence is evidence of the site-specific nature of the interaction.

EXAMPLE 5

Marker-ligand-dependent Biotinylation of a CEA-Expressing Cell Type a. Biotinylation by biotin tyramine of the HeLa-CEA expressing cells grown on slides.

Thawed HeLa-CEA slides which had been rehydrated in PBS for 10 minutes at room temperature were incubated for 15 minutes with streptavidin in PBS at 5 μg/ml. Slides were washed four times in PBS and then incubated for 15 minutes with in PBS at 10 μg/ml. Slides were washed 4 times in PBS and then incubated in block consisting of 1% BSA PBS containing 10% normal mouse serum for 30 minutes. Block was removed and the slides then incubated with CEA6 purified phage (as described in Example 1) at approximately $1\times10^{10}$ per ml in 1% PBS-BSA overnight at 40° C. Control slides were incubated under the same conditions with purified fluorescein-binding phage which do not recognise CEA.

Slides were moved back to room temperature and washed in PBST for 10 minutes, followed by incubation with 9E10-biotin at 3 μg/ml diluted in 1% BSA-PBS-for 1 hour. Washing was carried out for 10 minutes in PBST and the slides then incubated with ABC-HRP (DAKO) diluted 1:100 in PBS for 30 minutes. Slides were either developed at this point or washed three times in PBST, then incubated in either with biotinylated tyramine in 50 mM Tris-HCl pH 7.4 containing 0.03% $H_2O_2$ for 10 minutes. Three PBST washes were carried out and the slides then incubated with the ABC-HRP complex again for 30 minutes. Slides were developed using carbazole. Carbozole was prepared freshly by dissolving 9-amino-ethyl-carbozole (Sigma) at 60 mg per 25 ml DMF then adding 100 μl of this to 1 ml sodium acetate pH 5.2. 5 μl of 30% $H_2O_2$ was then added and 100 μl of this mix added to each slide chamber. Development was left for 20 minutes and then the carbazole washed off with $dH_2O$.

Slides incubated with the CEA6 phage but without the biotin-tyramine amplification step showed faint red staining in regions blebbing from the HeLa-CEA cell surfaces, whereas the slides treated with the anti-fluorescein phage showed no such staining. Slides incubated with CEA6 phage and then subjected to a round of biotin tyramine treatment shown significantly stronger staining of the regions of CEA, demonstrating that proteins present in the region of CEA6 phage binding had been biotinylated and were able to amplify the colour reaction due to recruitment of more ABC-HRP complex.

EXAMPLE 6

Maker-ligand Dependent Biotinylation of CEA i. Biotinylation of CEA.

HeLa-CEA expressing cells grown in chamber flasks were blocked in MPBS for 2 hours at room temperature. 100 μl of an anti-CEA mouse Mab was then incubated on the-slides at a dilution of 1:100 in MPBS for 1 hour at room temperature. Control incubations were carried out in MPBS without the presence of the anti-CEA Mab. Slides were washed three times ir PBST followed by three washes in PBS. 100 μl of of a goat anti-mouse HRP-conjugated second antibody (Pierce) was then aided at a dilution of. 1:2500 in MPBS and incubated for 1 hour at room temperature. Washing was carried out as before and 100 μl of biotinylated tyramine in 50 mM tris-HCl pH 7.4 with 0.03% $H_2O_2$ was added to each slide chamber for 10 minutes at room temperature. Cells were then scraped off the slides. Cells were pelleted at 600 rpm for 5 minutes and then resuspended in 10 mM triethanolamine, 1% triton in saline. Cells were left on ice for 10 minutes, then cell nuclei were pelleted at 13000 rpm in a minifuge for 5 minutes at 4° C. Supernatants were added to reducing protein loading buffer. and run on 10–15% SDS gradient PHAST gels. Protein were transferred to Hybond C extra (Amersham) membranes using the PHAST system programme at 70° C. for 30 minutes. Membranes were blocked for 2 hours in MPBS and incubated for 1 hour at room temperature with either a strepavidin-HRP complex, or an anti-CEA mouse Mab. Blots probed with the anti-CEA mab were washed three times in PBST followed by three washes in PBS, then incubated with an anti-mouse-HRP-conjugated antibody at a diltuion of 1:2500 in MPBS for 1 hour at room temperature. Blots were washed as before and developed using the ECL (Amersham) detection kit.

The western blot probed with streptavidin-HRP conjugate showed the presence of one major high molecular weight band in the Hela-CEA cells treated with anti-CEA, anti-mouse-HRP and then biotinylated tyramine. This band was shown to be reactive with an anti-CEA Mab. The band was a higher molecular weight than that theoretically anticipated for CEA, probably due to the many carbohydrate groups on CEA which result in retarded migration of the CEA. Two other biotinylated minor bands could be detected at round the expected size for a Mab or conjugated Mab. These bands could potentailly be biotinylated forms of the anti-CEA Mab and the anti-mouse-HRP conjugate. No other clear bands could be seen on the blot, although some some less specific biotinylation may be indicated by the presence of a high molcular weight smear after a long exposure (20 minutes) of the blot to ECL (Amersham) film in the lane corresponding to the Hela-CEA cells which were treated with both antibodies and the BT. Control lanes, in which treatment of the cells with BT or with the anti-CEA Mab was omitted, showed no evidence of biotinylation. This demonstrates the ability of the biotin tyramine system to selectively "tag" proteins binding in close proximity to a marker ligand to allow their detection and facilitate their purification.

EXAMPLE 7

Selection of Human Anti-E-selectin-binding Phage from a Large scFv Library a. Conjugation of polyclonal anti-E selectin IgG to HRP Polyclonal anti-human-E-selectin IgG was obtained from R and D Systems. The conjugation was carried out using a hydrogen peroxidase conjugation kit supplied by Pierce. 1 mg of maleimide-activated HRP was conjugated to 100 $\mu$g of Mab using the SATA protocol (Pierce). 20 $\mu$l of a 4 mg/ml SATA solution made up in DMF was added to 100 $\mu$l of polyclonal IgG in PBS. This was incubated for 30 min at room temperature, then 100 $\mu$l of deacetylation solution (Pierce) was added and incubation was continued for a further 2 hours at room temperature. Deacetylated IgG was separated from unreacted and deacetylated SATA on a 5 ml sepharose 25 column which had been pre-equilibriated with maleimide conjugation buffer. 0.5 ml fractions were collected and the majority of the protein was collected in fractions 2 and 3. 1 ml of the deacetylated IgG was then added to 1 mg of maleimide-activated HRP and incubated at room temperture for 1 hour.

b. Cell culture

Human vascular endothelial cells (HUVECs) (Clonetics) were cultured to passage 3 on 24 well plates (Nunc) coated with 1% gelatin. The cells were grown to approximately 80% confluence using EGM medium (Clonetics). HUVEC cells express a low basal level of the adhesion protein E-selectin.

c. Selection procedure Cells were washed with PBS and the cells were then incubated overnight at 4° C. in 200 $\mu$l of PBS/1% BSA in the presence of $1 \times 10^{12}$ phage prepared from a large non-immunised human scFv library. To one culture well a 1:20 dilution of the HRP-conjugated polyclonal anti-E selectin IgG was also added to the phage. Cells were washed three times in 0.5 ml PBST and three times in PBS. 200 $\mu$l of the biotin tyramine mix (as in Example 2 part bi) was added to each well and left for 10 minutes at room temperature. Cells were washed as before and the phage then eluted in 200 ml triethylamine (TEA) for 10 minutes at room temperature. The TEA was then neutralised with 100 $\mu$l of 1M TrisHCl pH 7.4.

d. Recovery of biotinylated phase

20 $\mu$l of streptavidin-coated magnetic beads (Dynal) were taken out of solution using a magnet and blocked for 2 hours at room temperature on a rotating platform with 1 ml of 3% MPBS. Beads were pelleted and 300 $\mu$l of eluted phage with 60 $\mu$l of 15% MPBS were added to the blocked beads and rotated for 15 minutes at room temperature. Beads were pelleted, washed three times in 1 ml PBST and three times in 1 ml PBS. The beads were resuspended in a final volume of 100 $\mu$l PBS. 50 $\mu$l of this was taken and used to directly infect 5 ml of an exponentially growing culture of E coli TG1 at 37 ° C. for 1 hour with light aeration in 2TYAG medium. Infected TG1s were plated on 2TYAG medium in 243 mm×243 mm dished (Nunc). Dilutions of bacteria were also plated out and incubated at 30° C. overnight. Colony counts gave the phage output titre.

Output titres for selections:

|  | Total eluate | Captured phage | % phage captured |
|---|---|---|---|
| Minus anti-E-sel-HRP conjugate | $8 \times 10^4$ | 81 | 0.10 |
| Plus anti-E-sel-HRP conjugate | $1.6 \times 10^4$ | 498 | 3.11 |

The percentage of biotinylated phage captured on the beads in the presence of the HRP-conjugated polyclonal anti-E selectin IgG is around 30-fold higher than the percentage captured in the absence of the antibody. This suggests the HRP-anti-E-selectin polyclonal IgG is targeting the biotinylation of E-selectin-specific phage.

e. Growth of single selected clones for soluble ELISA to identify anti-E-selectin scFv Single colonies were grown up exactly as described in Example 2 part c and the ELISAs were carried out as in part d, except that the plates were coated with 1 $\mu$g/ml recombinant E selectin (R and D Systems).

The number of positives screened from each round of selection and the number of P-selectin positive clones are shown below.

|  | No. clones | E-sel + ve | % E-sel + ve |
|---|---|---|---|
| Minus anti-E sel HRP conjugate | 95 | 0 | 0 |
| Plus anti-E sel HRP conjugate | 282 | 8 | 2.8 |

The ELISA results demonstrate the increase in the number of E-selectin binders selected for in the presence of the polyclonal anti-E selectin HRP conjugate compared to the selection when this antibody is omitted. This demonstrates that the antibody-HRP conjugate is responsible for the specific biotinylation of phage binding in close proximity to it.

EXAMPLE 8

Selection of Novel TGFβ1-binding Phage Using an Existing Anti-TGFβ1-Specific scFv 31G9 is a high affinity ($1.2 \times 10^{-9}$ M) anti-TGFβ1-specific scFv which was previously isolated from a large human non-immunised scFv phage display library by direct selection of the library on immobilised TGFβ1 The antibody does not recognise a neutralising epitope of TGFβ1. Investigations were carried out to assess whether a HRP-conjugate of 31G9 could be used in a signal transfer selection to isolate new lineages of phage antibodies which recognise different, potentially neutralising epitopes of TGPβ1.

a. Conjugation of 31G9 scFv to HRP.

31G9 was conjugated to maleimide-activated HRP as described-in Example 7, part a, except that 300 $\mu$g of purified scFv was used in the conjugation reaction.

b. Preparation of a low density TGFβ1 BiaCore chip.

50 μl of NHS/EDC reagent (Pharmacia) was incubated for 30 min at room temperature on the surface of a CM5 chip. The chip was washed 5 times in HBS and 75 ng of TGFβ1 in 75 μl of 10 mM sodium citrate buffer pH 3.6 was then incubated on the chip for 1 hour at room temperature. The chip was washed 5 times in HBS and then treated with 1M ethanolamine pH 8 for 10 min. The chip was stored at 4° C. in HBS. Approximately 40 resonance units (RUs) of TGFβ1 were linked to the chip.

c. Selection procedure.

i) First round of selection.

100 μl of HRP-conjugated 31G9 (approximately 30 μg) was incubated on the TGFβ1-coupled BiaCore chip for 1 hour at room temperature. The chip was washed 3 times in PBST and 3 times in PBS and 1×10$^{12}$ phage prepared from the human non-immunised library were then incubated on the chip surface for 1 hour at room temperature. The chip was washed as before and 100 μl of biotin tyramine mix (as described in Example 2 part bi) was incubated on the chip for 10 min at room temperature. The chip was washed as before and phage eluted from the chip using 200 μl of triethylaime TEA. The TEA was neutralised with 100 μl of 1M Tris-HCl pH 7.4.

ii) Recovery of biotinylated phage

20 μl of streptavidin-coated magnetic beads (Dynal) were taken out of solution using a magnet and blocked for 2 hours at room temperature on a rotating platform with 1 ml of 3% MPBS. Beads were pelleted and 300 μl of eluted phage with 60 μl of 15% MPBS were added to the blocked beads and rotated for 15 minutes at room temperature. Beads were pelleted, washed three times in 1 ml PBST and three times in 1 ml PBS. The beads were resuspended in a final volume of 100 μl PBS. 50 μl of this was taken and used to directly infect 5 ml of an exponentially growing culture of *E coli* TG1 at 37° C. for 1 hour with light aeration in 2TYAG medium. Infected TG1s were plated on 2TYAG medium in 243 mm×243 mm dished (Nunc). Dilutions of bacteria were also plated out and incubated at 30° C. overnight. Colony counts gave the phage output titre.

iii) Second round of selection.

Colonies were scraped off the 243 mm×243 mm plates into 3 ml of 2TY broth and 15% (v/v) glycerol added for storage at −70° C. Glycerol stock solutions from the first round of selection of the repertoire on the TGFβ1-BiaCore chip were rescued using helper phage to derive phagemid particles for the second round of selection. 250 μl of glycerol stock was used to inoculate 50 ml 2YTAG broth, and incubated in a 250 mL conical flask at 37° C. with good aeration until the OD600 nM reached 0.7 (approximately 2 hours). M13K07 helper phage (moi=10) was added to the culture which was then incubated stationary at 37° C. for 15 minutes followed by 45 minutes with light aeration (200 rpm) at the same temperature. The culture was centrifuged and the supernatant drained from the cell pellet. The cells were resuspended in 50 ml prewarmed 2YTAK, and the culture incubated overnight at 30° C. with good aeration. Phage particles were purified and concentrated by PEG precipitation (Sambrook et al., 1990) and resuspended in PBS to 10$^{13}$ tu/ml.

The second round of selection and capture of biotinylated phage on the TGFβ1-BiaCore chip was carried out exactly as the first round. The phage output titres are shown below.

| | Total output | Strepavidin captured-output | % captured |
|---|---|---|---|
| Round 1 | 2.5 × 10$^7$ | 5 × 10$^5$ | 2 |
| Round 2 | 6 × 10$^{10}$ | 1.8 × 10$^5$ | 0.5 | d. Growth of single selected clones for soluble ELISA to identify anti-TGFβ1 scFv Single colonies were grown up exactly as described in Example 2 part c and the ELISAs were carried out as in part d, except that the plates were coated with 0.2 μg/ml recombinant TGFβ1 (R and D Systems). The 192 clones from the second round of selection were screened by ELISA and 26 were found to be TGFβ1 positive (13.5%).

e. Sequencing of anti-TGFβ1scFv Antibodies

The nucleotide sequences of the anti-TGFβ1 antibodies were determined by first using vector-specific primers to amplify the inserted DNA from each clone. Cells from an individual colony on a 2YTAG agar plate were used as the template for a polymerase chain reaction (PCR) amplification of the inserted DNA using the primers pUC19reverse and fdtetseq. Amplification conditions consisted of 30 cycles of 94° C. for 1 min, 55° C. for 1 min and 72° C. for 2 min, followed by 10 min at 72° C. The PCR products were purified using a PCR Clean-up Kit (Promega) in to a final volume of 50 μl H$_2$O. Between 2 and 5 μl of each insert preparation was used as the template for sequencing using the Taq Dye-terminator cycle sequencing system (Applied Biosystems). The primers mycseq10 and PCR-L-Link were used to sequence the light chain of each clone and PCR-H-Link and pUC19reverse to sequence the heavy chain.

Sequencing revealed that a total of six different anti-TGFβ1 antibodies had been isolated by the signal transfer selection method using the 31G9-HRP conjugate to target the site specific biotinylation. These six antibodies were of VH germlines different from that of 31G9, as shown below.

| CLONE | VH GERMLINE | VL GERMLINE |
|---|---|---|
| ST3 | VH3 DP53 | VLambda2 DPL11 |
| ST6 | VH3 DP53 | VLambda3 DPL16 |
| ST10 | VH3 DP53 | VLambda3 DPL12 |
| ST14 | VH3 DP53 | VLambda2 DPL12 |
| ST19 | VH3 DP53 | VKappa1 DPK9 |
| ST21 | VH3 DP53 | VLambda2 DPL12 |
| 31G9 | VH3 DP49 | VKappa1 DPK9 |

All the clones selected had the same VH3 DPS3 germline paired with a variety of VL gene segments. ST6 and ST10 had the same VL germline and differed from each other at a single amino acid residue in VL CDR2. ST14 and ST21 also had the same VL germline but differed from each other at a single amino acid residue in VL CDR3. None of the selected clones had the same VH as 31G9. Clone ST19 had the same germline VL as 31G9 with a single amino acid change in VL FR2.

Overall this demonstrates the ability of the signal tansfer selection technique to select away from an undesired antigenic epitope and generate new lineages of phage antibodies which may have altered specificities.

EXAMPLE 9

Selection of Anti-chemokine Receptor Phage Using a Chemokine Ligand to Guide Selection The chemokine receptor CC-CKR5 is a co-receptor for macrophage tropic HIV-1 strains which is expressed on CD4[5] lymphocytes. CC-CKR-5 responds to a number of chemokines, including macrophage inflammatory protein (MIP)-1α. MIP-1α also binds to other chemokine receptors, including CC-CKR1 and CC-CKR4. MIP-1α may be used to guide signal transfer selection of phage antibodies or other phage displayed proteins which bind to the CC-CKR5 receptor a. Preparation of human CD4+ cells from blood.

Mononuclear cells were prepared from a 50 ml buffy coat using Ficoll-Paque (Pharmacia) density gradient centrifugation (600 g for 20 min at 20° C.). CD4+ cells were then isolated from the $1.5 \times 10^8$ recovered cells using a Biotex CD4 column, following the manufacturer's instructions, although PBS /2% foetal calf serum (FCS) was used throughout. Eluted cells were pelleted at 600 g for 5 min and resuspended in 300 μl PBS/2% FCS. $8.3 \times 10^6$ cells were recovered using this procedure. The recovered cells were analysed by flow cytometry and approximately 59t of the cells were found to be CD4+.

b. Selection procedure and capture of biotinylated phage.

$1 \times 10^5$ CD4+lymphocytes were incubated with $2 \times 10^{12}$ phage prepared from the $1.4 \times 10^{10}$ scFv phage display library in either the presence or absence of biotinylated MIP-1α (R and D Systems) at a final concentration of 375 nM. The final volume for each selection was made up 40 μl with PBS containing 2% marvel (MPBS). Selections were incubated for 14 hr at 4° C. Cells were pelleted by centrifugation at 600 g for 3 min, and washed in 1 ml MPBS. A total of three washes were carried out. 100 μl of streptavidin-HRP was added at a dilution of 1:1000 in MPBS. This was incubated for 2 hr, then washed as before. Biotin tyramine was then added (as Example 2, part bi) in 100 μl of 150 mM NaCl/50 MM TrisHCl pH 7.4 containing 3% $H_2O_2$ and incubated for 10 min at room temperature. Cells were washed and resuspended in 100 μl TE containing 0.5% triton. Biotinylated phage were captured on 10 μl of MPBS-blocked streptavidin-coated magnetic beads (Dynal). The beads were washed three times in 1 ml PBS/0.1% Tween 20 (PBST), then resuspended in 100 μl of PBS. Phage eluate before and after streptavidin capture were tiered by infection of an exponentially growing culture of E coli TG1 at 37° C. for 1 hr. The numbers of phage recovered from the various selection procedures are shown below.

| Selection No. phage No. Captured | Bio-MIP-1α % phage Bio-tyramine Captured | Strep-HRP Eluted | Total No. | |
|---|---|---|---|---|
| 1 | + | + | $3.7 \times 10^5$ | $5.9 \times 10^3$ |
| 1.6 | | | | |
| 2 | + | − | $4.0 \times 10^5$ | $8.0 \times 10^2$ |
| 0.2 | | | | |
| 3 | − | + | $4.9 \times 10^5$ | $1.4 \times 10^3$ | 0.3 |

The greatest recovery of biotinylated phage was observed from CD4+ lymphocytes incubated with both the biotinylated MIP-1α and biotin tyramine. Omission of either the biotinylated ligand or the biotin tyramine resulted in an approximately 5 to 6-fold drop in the percentage of phage recovered from the eluate. These results suggest the biotinylated MIP-1α is capable of binding the CD4+ cells in the presence of the phage library and directing biotinylation of phage binding around it in the presence of HRP and hydrogen peroxide.

c. Phage ELISA to identify CD4+ cell binders, CC-CKR5 transfected cell binders and CC-CKR5 amino terminal peptide binders.

Selected phage were analysed by phage ELISA for their ability to recognise CD4+ lymphocytes, a CC-CKR5 transfected cell line (provided by M. Parmentier and G. Vassart, University of Brussels) and a BSA-conjugated peptide corresponding to the amino terminal twenty amino acids of the CC-CKR5 receptor (MDYQVSSPIYDINYYTSEPC). Phage ELISAs were carried out as follows: individual clones were picked into a 96 well tissue culture plate containing 100 μl 2YTAG. Plates were incubated at 17° C. for 6 hours. M13KO7 helper phage was added to each well to an moi of 10 and incubated with gentle shaking for 45 min at 17° C. The plates were centrifuged at 2000 rpm for 10 min and the supernatant removed. Cell pellets were resuspended in 100 μl 2TYA with kanamycin (500 μg/ml) and incubated at 30° C. overnight. The ELISA was then carried out as for soluble ELISA (Example 2) except that in place of the 9810 a goat anti-M13 antibody was used at a dilution of 1:2500, followed by an anti-goat alkaline phosphatase conjugate, also at a dilution of 1:2500. $1 \times 10^5$ cells per ELISA well were used and the peptide BSA conjugate was coated at a concentration of 1 μg/ml.

30/95 of the phage selected in the presence of biotin tyramine and MIP-1α recognised CD4+ lymphocytes. 11/95 of the phage selected in the absence of MIP-la recognised CD4+ lymphocytes. 13 of the 30 clones which were positive on CD4+ cells were also found to be positive on the CC-CKR5 cell line. Of these two clones (RK-1 and RK-2) selected in the presence of MIP-1α and biotin tyramine were found to be specific for the CC-CKR5 peptide. The clones which do not recognise the CC-CKR5 peptide may of course recognise other epitopes of CC-CKR5, other MIP-1α receptors or proteins which are found on the cell surface in close proximity to MIP-1α receptors.

d. Sequencing of RK1 and RK2.

Sequencing of the two peptide binding clones was carried out as described in Example 2 part f. Clones RK1 and RK2 had identical VL gene segments.

| | VH family | VH segment | VL family | VL segment |
|---|---|---|---|---|
| RK1 | VH4 | DP67 | V13 | DPL16 |
| RK2 | VH4 | DP14 | V13 | DPL16 | e. Western blottinq using RK2

A representative of these peptide-binding clones (RK-2) was tested by western blotting on extracts from a CC-CKR5 transfected cell line and was found to bind to an approximately 35 kD band which may correspond to CC-CKR5.

This work describes the use of signal transfer selection co isolate phage antibodies of a desired specificity directly from a large phage library using a ligand of a known binding specificity (MIP-1α) as a marker to guide selection of phage binding in an area around the ligand binding site. A 1I proportion of the resultant selected population has been shown to be specific for the ligand's receptor (CC-CKR5). the antibodies generated in this example bind to a seven transmembrane protein which acts as a co-factor in HIV infection, hence the antibodies may have a therapeutic role.

EXAMPLE 10

Selection of Anti-chemokine Receptor Phage Using Light-activated Streptavidin and the Receptor Ligand to Guide As described in Example 9 MIP-1α can be used to guide selection of antibodies to at least one of its receptors (CC-CRK5). This example utilises the same system to demonstrate to ability of light activatible streptavidin to be used instead of biotin tyramine in an analogous signal transfer procedure.

a. Generation of light activatible streptavidin.

SAND (sulphosuccinimidyl 2-[m-azido-o-nitrobenzamido]-ethyl- 1,3-dithiopropionate, Pierce) is a photocrosslinking agent which is activated in the visible range (300–460 nm). SAND was linked to streptavidin by mixing 2 mg/ml streptavidin (Pierce) 7.5 mM SAND in PBS. This was incubated in the dark room at room temperature for 2 hr, then separated on a NAPS column.

b. Selection procedure $1 \times 10^5$ CD4+ lymphocytes were prepared as described in Example 9 part a and incubated with $2 \times 10^{12}$ phage prepared from the $1.4 \times 10^{10}$ scFv phage dsiplay library in either the presence or absence of biotinylated MIP-1α (R and D Systems) at a final concentration of 375 nM. The final volume for each selection was made up 40 μl with PBS containing 2% marvel (MPBS). Selections were incubated for 14 hr at 4° C. Cells were pelleted by centrifugation at 600 g for 3 min, and washed in 1 ml MPBS. A total of three washes were carried out. Cells were then incubated in the dark for 30 min with 500 mM streptavidin-conjugated SAND. Cells were washed as before, the exposed to 5 flashes of light from a standard flashgun. Cells were pelleted and resuspended in 100 μl TE containing 0.5% triton.

c. Captured of streptavidin-linked phage

The eluate was added to preblocked immunosorb tubed coated with 1 ml of 100 μg/ml biotinylated-BSA. After 1 hour the tube was washed lo times in 1 ml PBS. Phage which had been cross-linked to the streptavidin were eluted in 1 ml PBS containing 28 mM b-mercaptoethanol. Phage from the total eluate and from the captured population were titred. The numbers of phage recovered from the various selection procedures are shown below.

| Selection phage No. Captured | % phage | Bio-MIP-1α SAND | Strep Eluted | Total No. Captured | No. |
|---|---|---|---|---|---|
| 1 | + | + | $8.2 \times 10^4$ | 54 | 0.06 |
| 2 | + | − | $3.6 \times 10^3$ | 0 | 0 |
| 3 | − | + | $4.4 \times 10^5$ | 0 | 0 |

Phage were only recovered from the final eluate when streptavidin-SAND was included in the selection scheme. In the absence of this no background phage were recovered. These results deomstrate the ability of biotinylated MIP-la and a light activatible streptavidin molecule to specifically cross-link streptavidin to phage binding around the site of MIP-1α binding.

c. Phage ELISA to identify CD4+ cell binders, CC-CKR5 transfected cell binders and CC-CKR5 amino terminal peptide binders.

Selected phage were analysed by phage ELISA for their ability to recognise CD4+ lymphocytes, a CC-CKR5 transfected cell line (provided by M. Parmentier and G. Vassart, University of Brussels) and a BSA-conjugated peptide corresponding to the amino terminal twenty amino acids of the CC-CKR5 receptor (MDYQVSSPIYDINYYTSEPC). Phage ELISAs were carried out as described in Example 9.

24/54 of the phage selected in the presence of biotin tyramine and MIP-1α recognised CD4+ lymphocytes. 15 of the 24 clones which were positive on CD4+ cells were also found to be positive on the CC-CKR5 cell line. Of these two clones (RK-3 and RK-4) were found to be specific for the CC-CKR5 peptide.

d. Sequencing of RK3 and RI4.

Sequencing of the two peptide binding clones was carried out as described in Example 2 part f.

| | VH family | VH segment | VL family | VL segment |
|---|---|---|---|---|
| RK3 | VH4 | DP14 | Vλ3 | DPL16 |
| RK4 | VH4 | DP14 | Vλ3 | DPL16 |

RK1, which was a clone generate by biotin tyramine signal transfer selection using MIP-1α as a guide molecule was identical to RK-3, with the exception of a single amino acid difference in the VL CDR3 This demonstrates the selectivity of the selection procedures; a virtually identical clone recognising the same CC-CKR5 region can be selected by either biotin tyramine or light activatible-streptavidin signal transfer selection from a background of $1.4 \times 10^{10}$ other clones.

EXAMPLE 11

Selection of Phage Antibodies to Two Different Cell Surface Adhesion Molecules Using a Biotinylated Ligand Which Binds to Both to Guide Selection E and P selectin are cell adhesion molecules which are expressed on the surface of human vascular endothelial cells (HUVECs). E and P selectin are upregulated after stimulation with thrombogenic or inflammatory agents such as TNFα. The ligand for both these selectin has been found to be sialyl Lewis X, and this ligand has been used to generate antibodies to both of its receptor adhesion molecules in the same selection.

a. Stimulation of HUVEC's using TNFα.

HUVEC's (grown to passage 5) were stimulated with TNFα at 500 pg/ml for 4 hours and flow cytometry analysis was carried out to ensure that E selectin was up-regulated. After stimulation 43.8 percent of the cells treated gave a fluorescence value greater than 1, whereas without stimulation only 2.6 percent of the cells gave fluorescence greater than 1.

b. Biotinylation of sialyl Lewis X.

Sialyl Lewis X (Oxford Glycosystems) was biotinylated using biotinylated diaminopyridine (BAP). 1 mg BAP was dissolved in 50 μl pyridine/acetic acid (2:1 v/v). This was added directly to the dry carbohydrate (100 μg) and incubated for 1 hour at 60° C. The oligosaccharide-BAP adducts were reduced by the addition of 50 μl of 2.1M/l borane dimethylamine in pyridine/acetic acid and vortexed. Incubation was then carried on for a further hour at 80° C.

c. Selection and capture of biotinylated phage.

Stimulated HUVEC's were incubated with phage rescued from the large non-immunised scFv library. Two rounds of signal transfer selections were carried out in the presence or absence of 40 μg of biotinylated sialyl Lewis X. Phage were captured on streptavidin-coated magnetci beads as described in Example 1 part (e). The number of phage present before and after capture was titred. The greatest recovery of biotinylated phage was observed from stimulated cells when biotinylated sialyl Lewis X and biotin tyramine steps were present (1.8% recovery). Omission of either the biotinylated sialyl Lewis X or biotin tyramine resulted in an approximately 10-fold drop in the % of phage recovered from the eluate (both gave 0.2% recovery). These results suggest that biotinylated sialyl-Lewis X (with streptavidin-HRP) is capable of binding to the stimulated HRVEC's in the presence of the phage library and directing biotinylation of phage binding around the ligand binding sites.

d. Soluble ELISA to identify E- and P-selectin binders.

Recovered phage were examined by soluble ELISAs [as described in Example 2 part(d)] for their binding to E and P selectin. 3.6% of the clones recovered from the first round of selection in the presence of biotinylated sialyl Lewis X and biotin tyramine were E selectin positive. None of the clones tested from selections carried out on unstimulated cells, or in the absence of ligand or biotin tyramine were E selectin positive. 2.8% of the clones recovered from the HRP-conjugated anti-E selectin IgG selections were found to bind E selectin, whereas in the absence of the HRP-conjugate no clones were found to be E selectin positive. From the second round of selection in the presence of sialyl Lewis X and biotin tyramine the number of clones found to be E selectin positive increased to 13.7%.

P selectin ELISAs were also carried out on the population of clones selected in the presence of biotinylated sialyl Lewis X and biotin tyramine on stimulated cells 50% of the E selectin binders were also found to recognised P selectin, which shares sialyl Lewis X as its ligand. In addition a further 2% were found to be P selectin specific.

A further 21% of the second round selected population were found to bind to stimulated HUVEC's by soluble ELISA. The clones found to bind E selectin were sequenced and a diverse population of E selectin binders were identified. A range of different germline VH's were selected. The VL's were less diverse; a total of 4 different germline segments were selected which had common CDR3's.

These selections demonstrate the ability of a natural ligand for a particular cell surface protein to direct selection of cell surface protein binding clones. A ligand which recognises more than one cell surface protein (in this case E and P selectin) can be used to guide selection of antibodies to either of its target proteins.

EXAMPLE 12

Measurement of the Distance Over Which Signal Transfer Using Biotin Tyramine May Occur The following experiment was designed to assess the distance over which biotinylation may occur using HRP and biotin tyramine. Bacteriophage are approximately 1 μm long filaments with three copies of the gene 3 protein at one end of the filament. The gene 3 protein provides a marker which can be used to localise HRP specifically to one end of the phage via a mouse anti-gene 3 antibody, followed by an anti-mouse-HRP conjugate. Biotin tyramine and hydrogen peroxide can then be added to the tagged phage to allow biotinylation of the phage around the site of the HRP activity. Phage can then be transferred to electron microscope grids and labelled with streptavidin-gold beads to visualise the extent of biotinylation.

a. Preparation of phage.

An oestradiol-binding phage (MT31C) was grown from a bacterial glycerol stock in 50 ml 2TY/2% glucose/1μg/ml ampicillin (2TYGA) for 6 hours at 37° C. M13KO7 helper phage (Stratagene) was added to the culture to a multiplicity of infection (moi) of approximately 10 (assuming that an OD 600 mm of 1 is equivalent to $5 \times 10^8$ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in So ml 2TYAK (2TY media supplemented with 100 μg/ml ampicillin and 50 μg/ml kanamycin), and the culture incubated overnight at 30° C. with good aeration (300 rpm). Phage particles were purified and concentrated by two polyethylene glycol (PEG) precipitations (Sambrook, J., Fritsch, E. F., and Maniatis, T. (1990). Molecular Cloning—A Laboratory Manual. Cold Spring Harbour, New York) and resuspended in PBS to $10^{12}$ transducing units (tu)/ml.

b. Biotinylation of phage.

Phage were diluted to an approximate concentration of $2 \times 10^{10}$ per ml in a total volume of 500 μl. 5 μl of mouse Mab directed agains the gene 3 protein were then added to the phage and incubated at room temperature for 1 hour. 5 ml of an anti-mouse-IgG-HRP conjugate (Sigma) were then added to the phage and incubated at room temperature for a further 1 hour. The phage were then treated with biotin tyramine by adding 50 μl of 1M Tris-HCl pH 7.4 to the phage mix, followed by 4 μl of biotin tyramine stock solution and 2 μl of hydrogen peroxide (Sigma). The reaction was allowed to proceed at room temperature for 10 minutes, and the biotinylated phage then stored at 4° C. overnight.

c. Streptavidin-gold labelling of biotinylated phage.

EM grids were blocked in 0.1% gelatin and phage samples then applied. The phage were then labelled with streptavidin-5 nm colloidal gold (Sigma) at an approximate concentration of $2 \times 10^{11}$ particles per ml. A number of images of the biotinylated ends of phages were generated. When the anti-gene 3 antibody was omitted no gold labelling of the phage ends could be observed.

d. Estimation of the distance over which biotinylation has occurred using this system.

Figure 2:
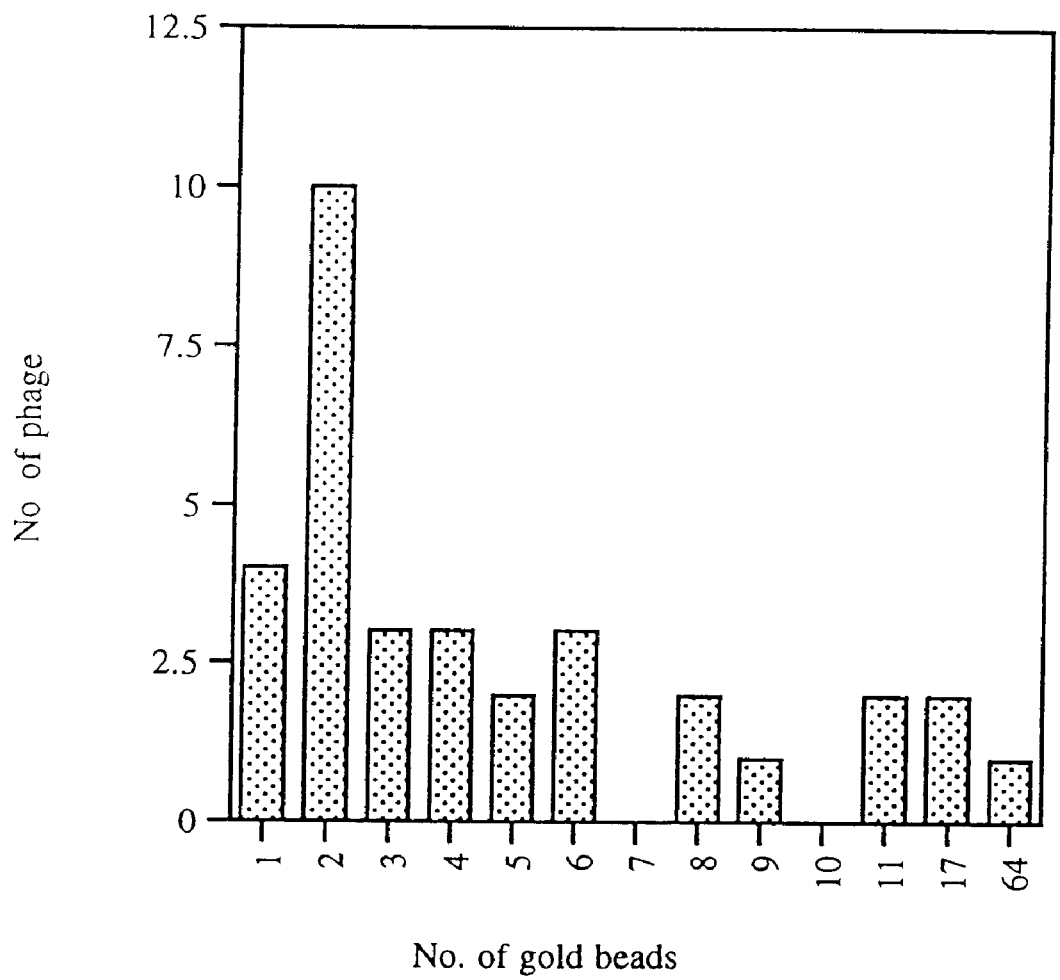
FIG. 2 illustrates results obtained in experiments described in Example 12, showing the distribution of gold paticles at the ends of page. For different numbers of beads per phage end the frequency is plotted. The average number of particles per phage was 6.6, the detected range 5 nm to 25 nm. The diameter of a globular protein is 4 nm.

The number of gold particles found to localise to individual ends of phages in the electron micrographs were counted and the data were used to generate a distribution histogram (FIG. 2). Data from two separate labelling experiments were pooled to generate the histogram. The average number of gold particles associated with the phage ends was found to be 6.6, giving an average radius of biotinylation of 7.2 nm. using this method the biotinylation range observed was from 5 nm to 25 nm, 5 nm being the limit of resolution of the experiment. A typical globular protein has a diameter of around 4 nm, hence the biotinylation range is of the order of 1 to 5 protein diameters.

e. Adjusting the distance of biotinylation.

To increase the distance over which biotinylation occurs HRP-conjugated molecules of various lengths may be used For example, a phage antibody with a specific binding characteristic may be HRP labelled and then used to guide the biotinylation of phage antibodies from the library. A phage particle is normally around lm long, hence this would give a radius of biotinylation of 10 nm to 1 μm. Similarly other molecules of shorter or longer lengths may be used e.g. streptavidin-dextran-HRP conjugates, or beads of defined sizes such as MACS beads (Miltenyi Biotec), which have a diameter of 50 nm and can be coupled either directly, or indirectly via biotin-streptavidin, to HRP. Iterations of the biotin tyramine reaction may be performed to broaden the area over which biotinylation is occurring. Example 10 describes a variation on the signal transfer technique which uses a light activatible streptavidin molecule with a short spacer arm (18 Angstrom). This procedure will only allow signal transfer to molecules binding immediately adjacent to the guide molecule.

EXAMPLE 13

Step-back Selection to Isolate Phage Antibodies Which Inhibit Ligand Binding

Figure 3:
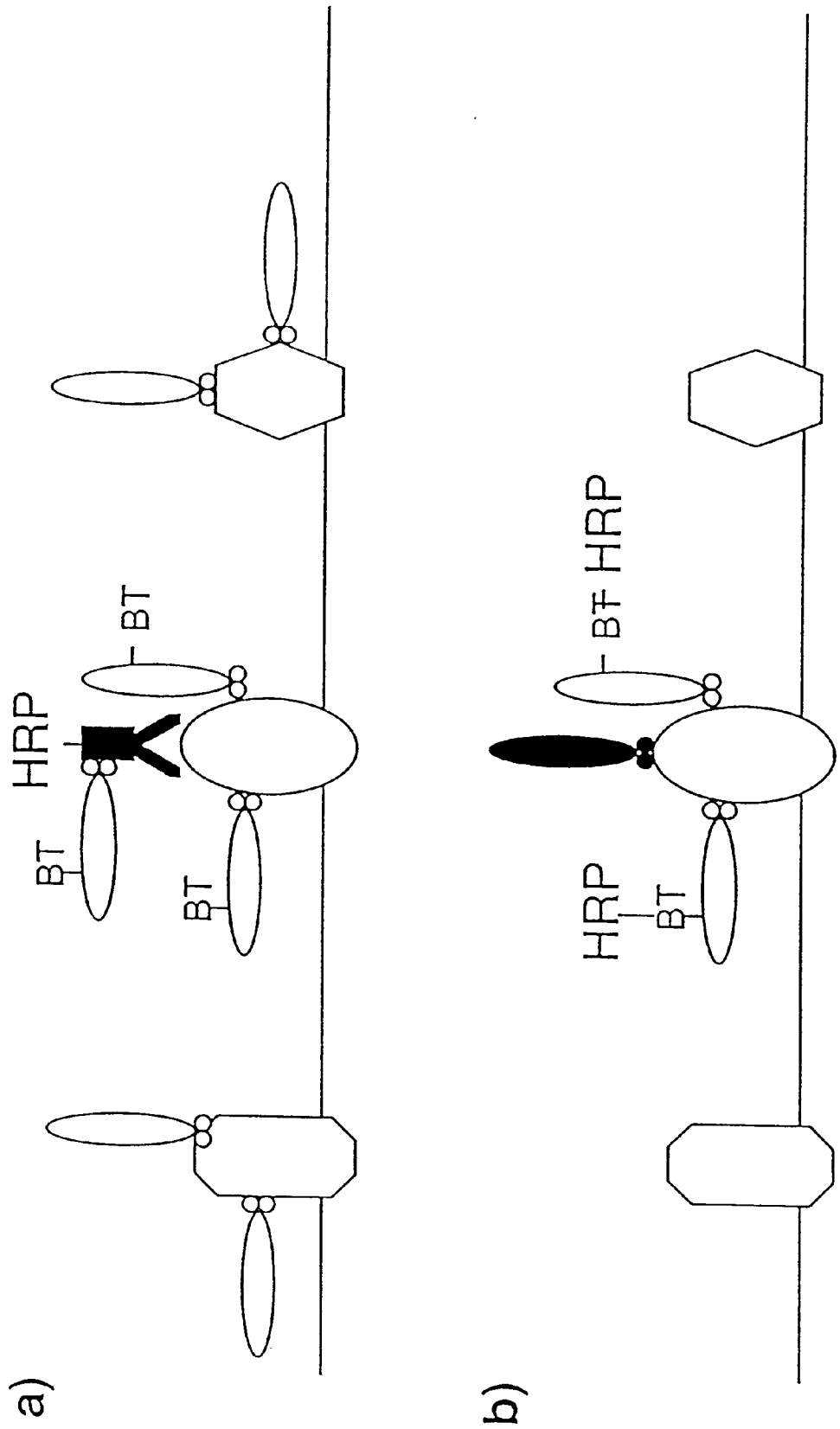
FIG. 3 illustrates a "step-back" selection scheme as exemplified experimentally in Example 13.

This example describes use of the biotin tyramine signal transfer selection procedure in a two step manner to isolate antibodies which inhibit binding of the initial marker ligand to cells. This procedure may be applied to the generation of inhibitors to any ligand, small molecule, or antibody. The process as exemplified here involves an initial first stage of the selection to biotinylate and capture phage antibodies which bind around the site of ligand binding. The biotinylated phage are then used directly (with no need for amplification) to guide a second stage of selection using cells in the absence of ligand. In this way antibodies which bind in the ligand binding site can be biotinylated by signal transfer procedure, then captured and screened for inhibition of ligand binding. Such a scheme is outlined in FIG. 3. The example described here uses phage to direct the second stage selection, but scFv may also be used either as a population of scFv molecules, or by individual clone isolation and purification, as may any other suitable binding molecule such as an antibody or binding fragments thereof. The system used in this example is the same as that described in Example 9. MIP-1α was used as the guide ligand on purified CD4+ lymphocytes.

a. First stage selection

CD4+ cells were purified from blood as described in Example 9 part a. The first stage selection procedure was then carried out exactly as described in Example 9 part b), except that phage were captured on 90 μl preblocked streptavidin-coated Dynal beads. After washing the beads were resuspended in 90 μl PBS and 30 μl removed to titre the phage present on the beads. The remaining 60 μl were again taken out of solution using the magnet and phage were eluted from the beads using 100 μl 100 mM triethlyamine for 10 minutes at 37° C., and then neutralised with 50 μl 1M Tris-HCl pH 7.4. After elution the beads were taken out of solution and the supernatant containing the biotinylated phage was taken for use in step two. The remaining beads were retained and used to infect $E$ $coli$ TG1 to ascertain the phage titre remaining on the beads after elution.

The following titres were obtained:

| | |
|---|---|
| Total number of phage captured on the Dynal beads: | $1.7 \times 10^4$ |
| Total number of phage retained on the beads after TEA elution: | $2.2 \times 10^3$ |
| Therefore total number eluted: | $1.5 \times 10^4$ | b. Second stage selection

The population of biotinylated phage which had been recovered from the first stage of the selection was added directly to $1 \times 10^6$ CD4+ lymphocytes in a total volume of 200 μl in MPBS. Phage were allowed to bind to the cells for 1 hr at room temperature, and cells were then washed 3 times in 1 ml PBS. Cells were pelleted at 4000 rpm for 2 min in a minifuge between washes. A further aliquot of the scFv phage library ($2 \times 10^{12}$ phage) was then added to the cells in 1 ml MPBS and allowed to bind for 1 hr at room temperature. Cells were washed 3 times in PBS as above and then resuspended in 200 μl MPBS containing 2 μl of streptavidin-HRP complex (Amersham). This was allowed to bind for 30 min at room temperature, and cells were then washed as before. Biotin tyramine treatment of the cells was carried out as described in Example 9 part b). Cells were then lysed by resuspension in 100 μl PBST and 30 μl preblocked streptavidin-coated Dynal beads were added to the lysate. Beads and lysate were rotated at room temperature for 20 min, and the beads then taken out of solution on a magnet. Beads were washed 3 times in 1 ml PBST, followed by 3 times in 1 ml PBS. Washed beads were used to directly infect an exponentially growing culture of $E$ $coli$ TG1. A total of around $4 \times 10^3$ clones were recovered from this selection procedure.

c. Growth of single selected clones for immunoassay.

Individual colonies from the second step of the selection procedure were used to inoculate 100 μl of 2TYGA into individual wells of tissue culture plates. Plates were incubated at 30° C. overnight with moderate shaking (200 rpm). Glycerol to 15% was added to each well and these master plates stored at −70C until ready for analysis.

d. Phage ELISA to identify anti-CD4+ scFv's.

Cells from the master plate were used to inoculate fresh 96 well tissue culture plates containing 100 μl 2TYGA per well. These plates were incubated at 37° C. for 6–8 hr. M13K07 was added to each well to an moi of 10 and incubated stationary for 30 min then 30 min with gentle shaking (100 rpm), both at 37° C. The plates were centrifuged at 2000 rpm for 10 min and the supernatant removed. Each cell pellet was resuspended in 100 μl 2TYAK and incubated at 30° C. overnight. Each plate was centrifuged at 2000 rpm for 10 min and the 100 μl of supernatant was recovered and blocked in 20 μl 18% M6PBS (18% skimmed milk powder, 6×PBS), stationary at room temperature for 1 hr.

CD4+ cells were isolated as described (Example 9, part a) and $1 \times 10^5$ cells were spun onto 96 well culture wells which had been precoated with poly-L-lysine for 30 min at room temperature. Cells were blocked in 100 μl MPBS for 2 hours at 37° C., and rinsed once in PBS. The phage supernatants were then added to the cells and incubated for 1 hr at room temperature, then washed 3 times in PBS. 100 μl of a 1:5000 dilution of sheep anti-fd antibody (Pharmacia) in MPBS was added and the plates incubated at room temperaure for 1 hr. Plates were washed 3 times in PBS and 100 μl of a 1:5000 dilution of donkey anti-sheep alkaline phosphatase conjugate (Sigma) in MPBS was added and incubated for 1 hr at room temperature. Plates were washed 3 times in PBS and alkaline phosphatase activity was visualised using the chromagenic substrate pNPP (Sigma). Absorbance was measured at 405 nm using a microtitre plate reader. 45 individual colonies were assessed for CD4 cell binding in this way, and 25 were found to be positive. 6 of these were taken at random for further analysis.

e. Assessment of anti-CD4 ecFv's to inhibit binding of MIP-1a to CD4+ cells.

6 scFv's were purified using nickel agarose metal affinity chromatography (Quiagen). $1 \times 10^5$ CD4 cells were preincubated with the purified CD4+-binding scFv's, or with an irrelevant control scFv for 1 hr at room temperature in PBS containing 0.1% BSA in a total volume of 100 μl. Approximately 5–10 μg of scFv was used per sample Cells were pelleted at 4000 rpm in a minifuge and washed once in 1 ml PBS. Biotinylated MIP-1α (R and D Systems) was made up according to manufacture's instructions 5 μl (equivalent to 5 ng) added to the cells in 100 μl MPBS and incubated at room temperature for 1 hr. Cells were washed as before. 100 μl of streptavidin-FITC (Sigma) at a dilution of 1:100 in MPBS was added and incubated for 30 min at room temperature, and cells were washed as before. Fluorescence was detected using a Coulter Epics-XL flow cytometer. MIP-la gave significant shift in the fluorescence of the cells when no scFv, or control scFv was added to the cells. In the presence of scFv from the selected clones MIP-1α binding to the cells was significantly inhibited. Inhibition varied from clone to clone.

EXAMPLE 14

Biotin Tyramine Selection in Solution Using a Peptide Phage Library

9E10 is a commercially available mouse monoclonal antibody which recognises a peptide which is part of the cellular myc protein (Munro, S. and Pelham, H. R. B. (1986), Cell 46, 291–300). This experiment was designed to select for peptides from a large peptide library which bind 9E10. 9E10 was conjugated to HRP to allow biotin tyramine-directed selection in solution. This can be considered as a novel method of epitope mapping antibodies, or other protein binding domains.

a. Construction of the peptide library

In this example, the peptide library used was constructed as described by Fisch et al (I. Fisch et al (1996) Proc. Natl. Acad. Sci. USA 93 7761–7766) to give a phage display library of $1 \times 10^{13}$ independent clones.

b. Conjugation of the anti-myc antibody (9E10) to HRP 1 ml of 1 mg/ml 9E10 IgG was conjugated to HRP using the Pierce EZ-link malemide activated HRP kit (cat no. 31494). 1 ml of 9E10 was added to the vial containing 6 mg of 2-mercaptoethylamine (MEA) in 100 µl conjugation buffer. This was incubated for 90 min at 37° C. The solution was allowed to cool to room temperature and the MEA was separated from the reduced IgG using the desalting column. The column was pre-equilibrated by washing with 30 ml of maleimide conjugation buffer and the 1.1 ml of IgG/MEA Solution was applied to the column. The conjugate was eluted using the maleimide conjugation buffer. 1 ml fractions were collected and fractions 5 and 6 were found to contain the majority of the protein. Fractions 7 and 8 contained smaller amounts of protein and were retained for control selections. Fractions 5 and 6 were pooled and 1 mg of maleimide activated HRP was added to the IgG and allowed to react for 1 hour at room temperature.

c. First round selections using 9E20-HRP and the peptide phage display library

Approximately $1 \times 10^{13}$ phage were used per selection. 6 µg of 9E10-HRP conjugate were added to the peptide phage in a total volume of 1 ml PBS with 2% marvel (MPBS). Control selections were also carried out using 6 µg of unconjugated 9E10. All selections were carried out in 1 ml. Phage and antibody were allowed to bind overnight at 4° C. 50 µl 1M Tris-HCl pH 7.4, 4 µl biotin tyramine and 2 µl hydrogen peroxide were then added to the selection and allowed to react for 10 min at room temperature. 100 µl of streptavidin-coated magentic beads (Dynal) which had been preblocked for 30 min in MPBS were then added to the selection and rotated at room temperature for 30 min. Magnetic beads were then brought out of solution using a magnet and washed with 3×1 ml of PBS containing 0.1% Tween, followed by washing with 3×1 ml of PBS. The beads were resuspended in a final volume of 100 µl PBS and used to directly infect 5 ml of an exponentially growing culture of *E. coli* TG1. Infection was carried out by incubation stationary at 37° C. for 30 min, followed by 30 min slow shaking (200 rpm) at 37° C. Phage were plated out on 2TY medium containing 100 µg/ml tetracyclin (2TYT). Colony counts gave the phage titre d. Second and third round selections using 9E10-HRP and the peptide library.

The plates were scraped into 5 ml of 2TY. 50 µl of this plate scrape was then added to 50 ml of 2TYT and grown overnight at 30° C. with aeration. 1 ml of the resultant cell suspension was pelleted at 6000 rpm in a minifuge and 100 µl of 10×MPBS added to the supernatant. 9E10-HRP conjugate, unconjugated were then added to the blocked phage as selections carried out exactly as the first round described in part c. above. The selection was repeated so that a total of three rounds of selection were performed. The number of phage recovered in the output populations at each round was as follows:

|  | 9E10-HRP | 9E10 |
|---|---|---|
| Round 1 | $5.2 \times 10^5$ | $2.0 \times 10^4$ |
| Round 2 | $1.2 \times 10^6$ | $5.9 \times 10^4$ |
| Round 3 | $8.0 \times 10^5$ | $2.6 \times 10^5$ | e. Screening the output populations for binding to 9E10

Individual colonies from the third round of selection were used to inoculate 96 well tissue culture plates containing 100 µl of 2TYT per well and clones were grown overnight at 30° C. with good aeration (300 rpm). Plates were centrifuged at 2000 rpm and the 100 µl from supernatant from each well was recovered and blocked in 20 µl 18% M6PBS (18% milk powder, 6×PBS) stationary at room temperature for 1 hour. ELISA plates which had been blocked overnight at 4° C. with 50 µl of 10 µg/ml 9E10, or 50 µl PBS alone were washed in PBS and then blocked for 2 hours stationary at 37° C. in 3MPBS. ELISA plates were washed in PBS and the blocked phage supernatants then added to the ELISA plate. The plates were incubated stationary at room temperature, then washed three times with PBST, followed by three washes with PBS. 50 µl of anti-gene 8-HRP conjugate diluted at 1:5000 in 3MPBS were then added to each well and the plates incubate at room temperature for 1 hour. Plates were washed as before and the ELISA developed for 1 hour at room temperature with 50 µl of TMB substrate. Development was stopped by the addition of 25 µl of 1M $H_2SO_4$.

f. Results of the screening 95 clones from the third round of selection using the 9E10-HRP conjugate, and 95 from the unconjugated 9E10 selection were screened by ELISA. 3 positives were identified as binding 9E10, but not PBS coated plates from the 9E10-HRP selection, whereas no positives were found from the control unconjugated 9E10 selection. The three positive clones were rechecked by ELISA as above on an unrelated mouse monoclonal antibody and did not give any signal, demonstrating that they bind specifically to the 9E10 Mab.

g. Sequencing 9E10-binding clones

Clones found to be positive for binding to 9E10 were analysed by DNA sequencing as described by Fisch et al. All three clones were found to be identical. None had a peptide insert in Exon 1, and all a 10 amino acid peptide sequence inserted in Exon 2 which had some homology to the myc tag, as shown below:

Selected sequence: P M P H A E G K S T
Myc tag: G A A E Q K L I S E E D L M

In summary 9E10-specific clones have been identified from the peptide library, which have some homology to the myc tag. This demonstrates that biotin tyramine selections can be successfully carried out in solution, and can be carried out on non-antibody libraries.

EXAMPLE 15

Characterisation of Clones Which Bind to CD4+ Cells, but Not to the Chemokine Receptor CC-CKR5, by Western Blotting and ICC Example 9 described the selection of phage antibodies which bind to a chemokine receptor. Phage selections were carried out on CD4+ cells using biotinylated MIP-1α, followed by streptavidin-HRP to guide the selection. ³⁰⁄₉₅ phage selected in the presence of the biotin tyramine and MIP-1α recognised CD4+ lymphocytes. 13 of these clones were found to be positive for the CC-CKR5 chemokine receptor for which MIP-1α is a ligand, leaving 17 clones which bind to CD4+ cells, but to another antigen to be discertained (Example 9 part c). These clones may recognise antigens which are normally found in close proximity to MIP-1α receptors, or are MIP-1α receptors other than CC-CKR5 (CC-CKR1 and CC-CKR4 both bind to MIP-1α). Identification of the antigens to some of these CD4+-binding clones allows examination of protein-protein interactions on the cell surface, and exemplifies the potential of biotin tyramine selection as a tool for discovering novel protein-protein interactions.

Three clones, CD4A2, CD4E1 and CD4D2 were chosen at random from the 17 CD4+ binding clones and were subjected to further analysis to identify their antigen partners. Initial studies involved probing western blots of membrane fractions prepared from CD4+ cells with purified scFv from the 3 clones. Immunocytochemistry on CD4+ cells was also carried out using the scFv's.

a. Preparation of CD4+ cell membrane fractions.

CD4+ lymphocytes were prepared as described in Example 9, part (a). Membrane preparations were then generated as follows. Approximately $1 \times 10^6$ cells were resuspended in 1 ml of 12 mM Tris-HCl, pH 7.5 in 250 mM sucrose. Cells were lysed by three cycles of freeze thawing, and the lysates were homogenised in a ground glass homogeniser. The homogenate was centrifuged at 270×g for 10 min at 4° C. to pellet the nuclear fraction. The supernatant was then centrifuged at 8000×g for 10 min at 4° C. to pellet the mitochondrial and lysosomal fractions. The final centrifugation to pellet the plasma membrane fraction was carried out at 100 000×g for 60 min at 4° C., and the membrane fractions were resuspended in 100 μl PBS and stored at −70° C.

b. western blotting of membrane fractions.

4–20% Novex gradients were run under non-reducing, denaturing conditions at 125V for 1.5 hr, and blotted in at 25V for 1.5 hr. Blotting was carried out in the Novex apparatus exactly as recommended by the manufacturers using Hybond-C membrane (Amersham).

c. Probing western blots.

Membranes were blocked for 45 min in MPBS and probed with 50 μg purified scFv in 5 ml MPBS for 1 hr at room temperature. Blots were washed in three changes of PBST, followed by three changes of PBS. 9E10 at a 1:100 dilution in MPBS was then incubated on the membrane for 1 hr at room temperature. Washing was carried out as before, and anti-mouse-IgG-HRP antibody then added at a dilution of 1:5000 in MPBS. Blots were developed using ECL substrate (Amersham) and exposed to autoradiographic film.
Clone CD4E1 gave a band of approximately 29 kDa
Clone CD4D2 gave a band of approximately 31 kDa
Clone CD4A2 failed to give a specific band under denaturing gel conditions.

d. Immunocytochemistry (ICC) using scFv'sf on CD4+ cells.

Approximately $1 \times 10^5$ CD4+ cells were spun onto poly-L-lysine subbed slides using a Cytospin (Serotech). Slides were blocked in MPBS for 2 hr at room temperature and a 1:10 dilution of the scFv in MPBS then incubated on the slides for 1 hr at room temperature. Slides were washed in PBS and detection was achieved using 1:100 dilution of 9E10, followed by a 1:500 dilution of anti-mouse-HRP, both diluted in MPBS and incubated for 1 hr at room temperature, with washing in PBS between incubations. CD4E1 and CD4D2 both gave clear staining of the cell membranes.

EXAMPLE 16

Demonstration of the Use of Signal Transfer Selection to Identify Novel Protein-Protein Interactions To definitively identify the antigens which clones CD4A2, CD4E1 and CD4D2 recognise, a lambda gt11 cDNA expression library was constructed from mRNA from purified CD4+cells and screened with purified ScFv's.

a. isolation of messenger RNA

Messenger RNA was purified from a population of CD4 purified cells using a QuickPrep Micro mRNA purification kit (Pharmacia). The mRNA was purified following manufacturer's instructions. The method involved lysis of the cells in a buffered aqueous solution containing guanidinium thiocyanate and N-lauroyl sarcosine, the extract was then diluted three fold with an elution buffer which reduces the guanadinium concentration to a level which is low enough to allow efficient hydrogen bonding between poly(A) tracts on the mRNA and the oligo (dT) attached to cellulose, but high enough to maintain complete inhibition of RNAses. The dilution step causes a number of proteins to precipitate, giving an initial purification The extract was clarified by short centrifugation at top speed in a minifuge and the supernatant transferred to a microcentrifuge tube containing Oligo(dT)-cellulose. After 10 min, during which time the poly (A)+RNA binds to the oligo (dT)-cellulose, the tube was centrifuged at high speed for 10 sec, and the supernatant was aspirated off the pelleted oligo (dT)-cellulose. Pelleted material was washed sequentially with 1 ml aliquots of high salt buffer and low salt buffer, each wash being accomplished by a process of resuspension and brief centrifugation. After the last wash the pelleted material was resuspended in 50 μl of low salt buffer and transferred to a MicroSpin column placed in a microcentrifuge tube, and the column was washed three times with 0.5 ml of low salt buffer. Finally, the polyadenylated materiel was eluted with prewarmed elution buffer (10 mM Tris-HCl (pH 7.5), 1 mM EDTA). The mRNA was precipitated by addition of a glycogen carrier, potassium acetate and ethanol. After precipitation the mRNA was recovered by centrifugation and resuspended in DEPC treated water.

b. cDNA Synthesis cDNA was synthesised from the CD4 mRNA using a cDNA synthesis kit supplied by Amersham International. The detailed protocol booklet was followed The 1st strand synthesis reaction contained hexamer primers and reverse transcriptase with mRNA as template. Second strand synthesis was carried out with Ribonuclease R and DNA polymerase, and after synthesis the ends of the cDNA were made blunt by treatment with T4 DNA polymerase. The cDNA was then purified by phenol/chloroform extraction.

c. Construction of cDNA library cDNA was cloned into the lambda gt11 expression vector using Amersham's cDNA rapid adaptor ligation module (RPN 1712) and the cDNA rapid cloning module—gt11 (RPN1714). Adaptors were added to the cDNA to give EcoR1 restriction cohesive ends, and cDNA with adaptors were separated from free adaptors by a column step. The adapted cDNA was then ligated into lambda gt11 vector then packaged using an in vitro packaging kit. Resultant reactions were titred to access the library size, which was found to be $7 \times 10^5$.

d. Screening the cDNA expression library with scFv

For immunoscreening host cells (Y1090) were infected with phage from the library and plated out on L top agarose. After 3.5 hours growth at 42° C., the plates were overlaid with nitrocellulose filters saturated with 10 mM IPTG, an inducer of Lac Z gene expression, and incubated for a further 3.5 hours at 37° C. During this time, the plaques are transferred to the filter along with the β-galactosidase fusion proteins, released from the lytically infected cells. The filters were carefully removed and washed briefly in PBS and then blocked in MPBST. Detection of positives was by sequential incubations with scFv of interest at a concentration of 10 μg/ml in MPBS, followed by 9E10 (1:100 in MPBS) and then an anti-mouse HRP conjugate (1:1000 in MPBS). The filters were washed between incubations in 3 changes of PBST Signal was detected using an Enhanced Chemiluminescent system (Amersham ECL Kit). Plaques which were found to be positive from the first round of screening were picked and re-infected into a fresh culture of Y1090, and the screening process repeated. This was carried out to ensure the reproducibility of the positive signal and to obtain clonal plaques.

e. Sequencing inserts from positive plaques.

Single plaques were picked into 100 μl SM buffer and left at 4° C. overnight. 5 μl of the eluted plaques was then taken and used as template for a standard 50 μl PCR reaction (0.5 μl TAQ Polymerase, 4 μl 10 mM dNTP, 5 μl 10×PCR buffer, 2.5 μl of each primer (10 μM), made up to 50 μl with water). Primers used for sequencing were

| gt11screen5 | 5' GAC TCC TGG AGC CCG |
| gt11screen3 | 3' GGT AGC GAC CGG CGC |

PCR products were then cleaned up and used in sequencing reactions as described previously (Example 2 part e), except that gt11screen5, and gt11screen3 were used as sequencing primers. Resultant nucleotide sequences were then aligned to the NCBI data base using the BLAST programme (Altschul et al., J. Mol. Biol. (1990) 215, 403–410.).

f. Results of the sequence alignments

| scFv clone | lambda gt11 clone | Homology | Degree of identity |
|---|---|---|---|
| CD4E1 | 2.1.1 | Rat CL-6 | 80% |
| CD4A2 | 3.1.1 | TRIP-4 (human) | 100% |
| CD4D2 | 10.1.1 | 26S proteosome p31 (human) | 100% |
| CD4E1 | | | |

This was found to recognise a lambda clone containing an insert which had homology to a rat protein called CL-6, which is an insulin-induced growth response protein. This protein is a protein tyrosine phosphatase (PTP). PTP's are a family of intracellular and integral membrane phosphatases which dephosphorylate tyrosine residues in proteins. PTP's have been implicated in the control of normal and neoplastic growth and proliferation. PTPs have also been implicated in T-cell signal transduction pathways, where they are involved in coupling receptors to the generation of second messenger inositol triphosphate. The DNA fragment isolated here has 80% identity at the nucleotide level with the rat CL-6 protein, and hence is probably the human homologue. CL-6 is an approximately 30 kDa protein.

The rat gene CL-6 was identified by R. H. Diamond et al. (1993, Journal of Biological Chemistry 268, 15185–15192) as a gene which was induced in regenerating liver and insulin-treated Reuber H35 cells, a rat hepatoma cell line which grows in response to physiological concentration of insulin and retains some properties of regenerating liver. CL-6 was one of a panel of 41 novel growth response genes identified in this study, and was found to be the most abundant insulin-induced gene CL-6 is induced as an immediate-early gene in the liver cells, and its immediate-early induction during liver regeneration suggests that it is regulated by early stimuli, and not by insulin alone. CL-5 mRNA expression was found to be highest in liver and kidney, but showed some expression in most tissues. The CL-6 protein is predicted to be highly hydrophobic, and may be a membrane-associated protein. CL-6 is likely to have a role in the tissue-specific aspects of cellular growth, involved in the maintenance of normal liver architecture or metabolism during regeneration and foetal development.

CD4A2

This clone was found to recognise thyroid receptor interacting protein 4 (TRIP4). Thyroid hormone receptors (TRs) are hormone-dependent transcription factors that regulate expression of a variety of specific target genes Thyroid interacting proteins are thought to play a role in mediating the TR's response to hormone binding.

CD4D2

This clone was found to recognise the p31 (31 kDa) subunit of the human 26S proteosome. Proteosomes are involved in the ubiquitin-dependent proteolytic pathway and in antigen processing, and there is evidence that they are found in close proxmity to, or associated with the plasma membranes in g. Summary of results It has been demonstrated that the signal transfer selection procedure can be used to select for antibodies, or other binding species, which bind to antigens found in the vicinity of the original target antigen, but which do not recognise the target antigen itself. CD4A2, CD4E1 and CD4D2 are three examples of this. The antigens which these three antibodies recognise have been identified by screening a cDNA expression library. The antigens identified by cDNA screening fit with the predicted sizes of the antigens which CD4 E1 and CD4D2 bind to on western blotting i.e. the human homology of CL-6 (30 kDa), the p31 subunit of the 26S proteosome (31 kDa). CDA2 recognises the TRIP4 protein, which has an estimated molecular weight of 32 kDa. The antibodies stain CD4+ cell membranes by ICC, as does MIP-la, the ligand for the CC-CKR5 receptor which was used to guide the signal transfer selection. Hence signal transfer selection has been used to identify a panel of antigens which are found in close proximity (probably up to 25 nm) to MIP-1a receptors on the surface of CD4+ cells. This is a demonstration of the use of signal transfer selection as a means of identifying novel protein-protein interactions, and to identify novel genes. The CL-6 gene has previously only been identified in rat, and signal transfer selection has enabled the cloning of the human homologue of CL-6.

EXAMPLE 17

Biotinylation of CD4E1 Phage on the Cell Surface Using MIP-1α to Direct the Biotinylation Clone CD4E1 has been selected by virtue of the fact that it binds to an antigen found close to MIP-la binding sites on CD4+ cell surfaces. It should therefore be possible to use biotinylated MIP-1α bound to streptavidin-HRP to catalyse biotin tyramine deposition onto CD4E1 phage bound co the CD4+ cell surface to demonstrate that the CD4E1 antigen is normally found in close association with MIP-1α receptors. This was tested by incubating cells with biotinylated MIP-1α, streptavidin-HRP and CD4E1 phage, treating with biotin tyramine and then recovering the biotinylated phage and titring. Recovery of phage using this system was compared to recovery when phage which bind at a site on the CD4+ cell surface which is remote from the MIP-1α binding sites were incubated with the cells, or when a biotinylated ligand (biotinylated VCAM) which binds at another remote site on the CD4+ cell surface was used in conjuction with CD4E1 phage.

a. Biotinylation of phage on the cell surface.

CD4+ cells were purified as described in Example 9. CD4E1 phage, or phage from a CD4+ binding clone (CLA4)

were prepared as described in Example 12. $1 \times 10^6$ cells were incubated for 1 hr with 5 ng of biotinylated MIP-1α, or 5 ng of biotinylated VCAM in a total volume of 100 βl PBS/BSA. Streptavidin-HRP (1:1000 dilution in PBS/BSA) was then added to the cells and incubated for 30 min. Cells were washed in PBS, and then $10^{11}$ phage added in PBS/BSA and allowed to bind to the cells for 1 hr at room temperature. Cells were washed in PBS and then treated with biotin tyramine as described before. Cells were washed in PBS and then lysed in PBS containing 0.1% Tween and biotinylated phage were captured on streptavidin-coated. Beads were washed three times in PBST and three times in PBS, then infected directly into an exponentially growing culture of *E coli* TG1.

b. Results of phase biotinylation.

The number of phage captured on beads was caluated from the titres. If no biotinylation reaction was carried out approximately $10^7$ CD4E1 and CLA4 phage were found to bind to the cell surface.

| Phage | Ligand | Total Number of phage recovered |
|-------|--------|--------------------------------|
| CD4E1 | MIP-1α | 2000 |
| CD4E1 | VCAM   | 800 |
| CD4E1 | —      | 400 |
| CLA4  | MIP-1α | 600 |
| CLA4  | VCAM   | 800 |
| CLA4  | —      | 200 |

The number of phage recovered was at least 2.5 times higher when CD4E1 phage was incubated with the MIP-1α, than the recovery attained in the various control samples. This provides indication that HRP-conjugated MIP-1α is able to specifically biotinylate CD4E1 phage because CD4E1 recognises an antigen which is found in close proximity (within 25 nm) to the MIP-1α receptor.

EXAMPLE 18

Use of Biotin Tyramine as a Signal Amplification Reagent in Flow Cytometry

Signal transfer can also be used as an amplification system for enhancing fluoresence signals in flow cytometry. This is achieved by allowing a HRP-conjugated antibody, or ligand to bind to cells. Cells can then be treated with hydrogen peroxide and biotin tyramine, as described for the selection procedure. This will cause biotin tyramine deposition around the antibody, or ligand binding site on the cell surface. Streptavidin-fluorescein (FITC) can then be added to the cells. This will bind to the newly deposited biotin on the cell surface and give an enhancement in signal as compared to a standard FITC cell labelling protocol using FITC-conjugated antibody or ligand. This has been shown to be the case by comparing the labelling achieved on purified CD4+ lymphocytes using either an anti-CD4+ antibody, followed by anti-mouse-FITC, or by using anti-mouse-HRP followed by biotin tyramine treatment and then streptavidin-FITC.

a. Cell labelling.

CD4+ lymphocytes were purified as described in Example 9. Cells were incubated with the anti-CD4+ antibody (Sigma), at a dilution of 1:1000 in PBS/BSA. Cells were washed in PBS, and then either of the two second antibodies (anti-mouse-FITC, or anti-mouse-HRP) were added to the cells, at a dilution of 1:1000 in PBS/BSA. $1 \times 10^5$ cells were used per sample. Cells were washed in PBS and either detected directly (anti-mouse-FITC), or treated with biotin tyramine as described previously. Biotin tyramine was added over a range of concentrations from 0.25 μg/ml up to 100 μg/ml, in order co determine the concentration at which the optimal signal enhancement occurred. After biotin tyramine treatment cells were again washed in PBS, then streptavidin-FITC was added at a diltuion of 1:1000 in PBS. Cells were analysed by flow cytometry.

b. Flow Cytometry Results

Figure 4:
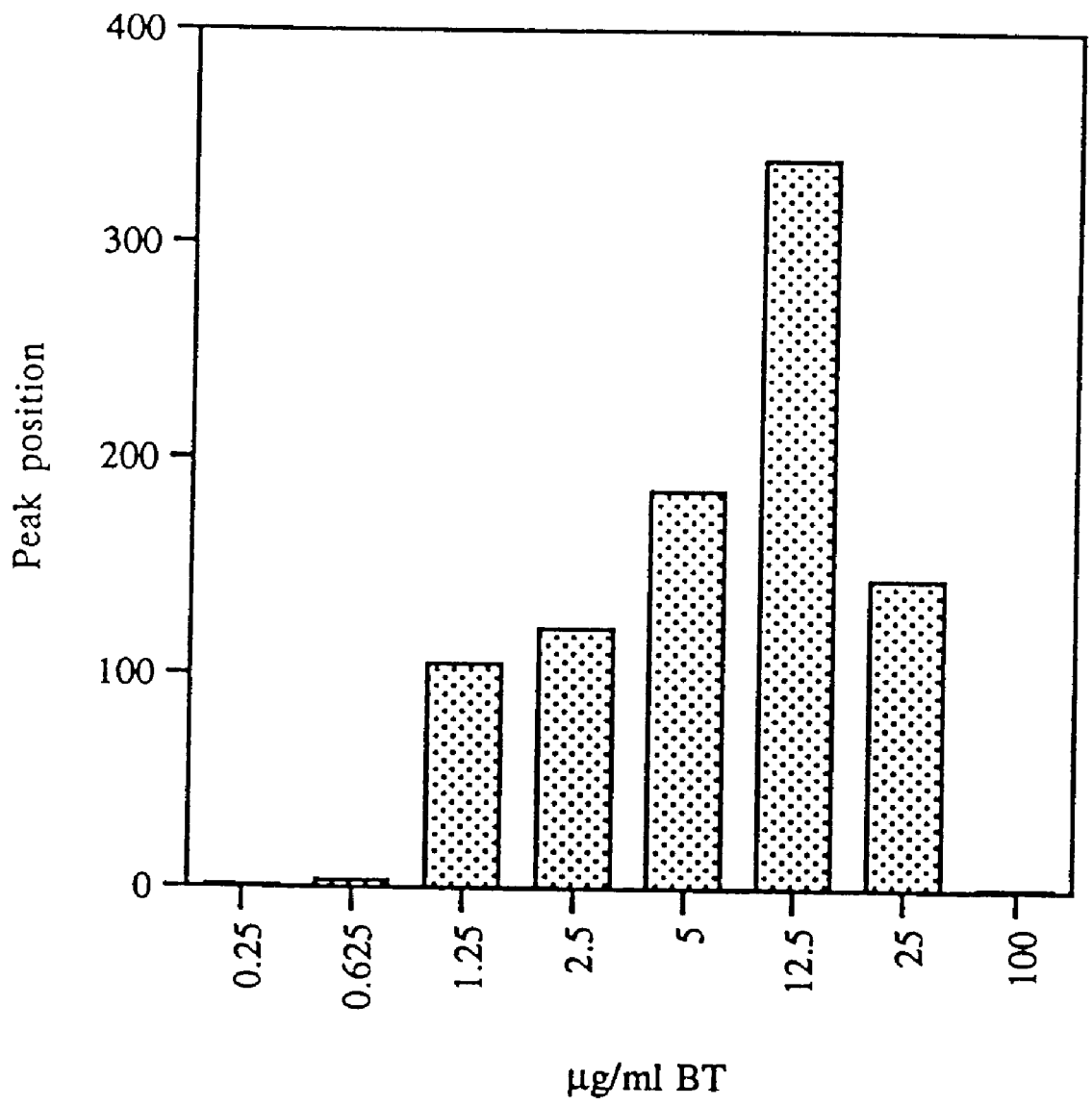
FIG. 4 shows results of flow cytometry experiments described in Example 18. The peak position (i.e. a measure of the fluorscence achieved) obtained using different biotin tyramine concentrations (in $\mu$g/ml) is plotted.

The peak position (i.e. a measure of the fluorscence achieved) obtained using the different biotin tyramine concentrations was plotted. The results are shown in FIG. 4. As can be seen from the figure, optimal enhacement with biotin tyramine was obtaining using a concentration of 12.5 μg/ml. The optimised peak position obtained using the anti-mouse-FITC second antibody was 60 fluorescence units, hence the use of biotin tyramine has efficiently enhanced this signal over 5-fold (from 60 to 330 fluorescence units).

EXAMPLE 19

Iteration of Biotin Tyramine Treatment to Give Further Signal Enhancement

Repeated rounds of biotin tyramine treament may be carried out before a final detection step, using streptavidin-FITC. The repeated rounds are achieved by an initial biotin tyramine treatment, followed by the addition of streptavidin-HRP and then a further biotin tyramine treatment. This example demonstrates the effective use of two rounds of biotin tyramine treatement to generate further signal enhancements. A mixed Ficoll purified cell preparation (containing monocytes, lymphocytes and granulocytes) and labelling with anti-CD36 antibody, which is a marker of monocytes, was used here as a model system.

a. Cell labelling.

Figure 5:
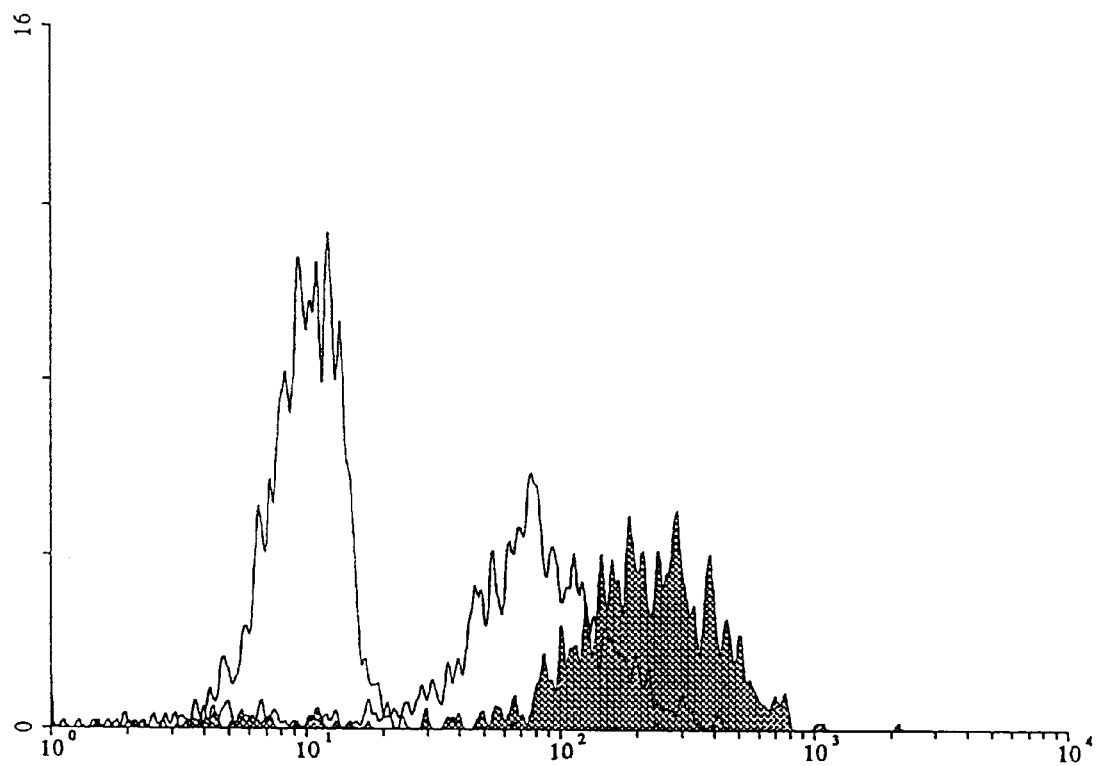
FIG. 5 shows the fluorescence shifts resulting from two flow cytometry readings, one for a sample subject to one biotin tyramine treatment, the other for a sample subject to reiteration, as described in Example 19. As can be seen, iteration of the biotin tyramine treament results in a 2.5 fold shift in the average fluorescence level of the cells. (Events plotted against FL1LOG.)
Figure 6:
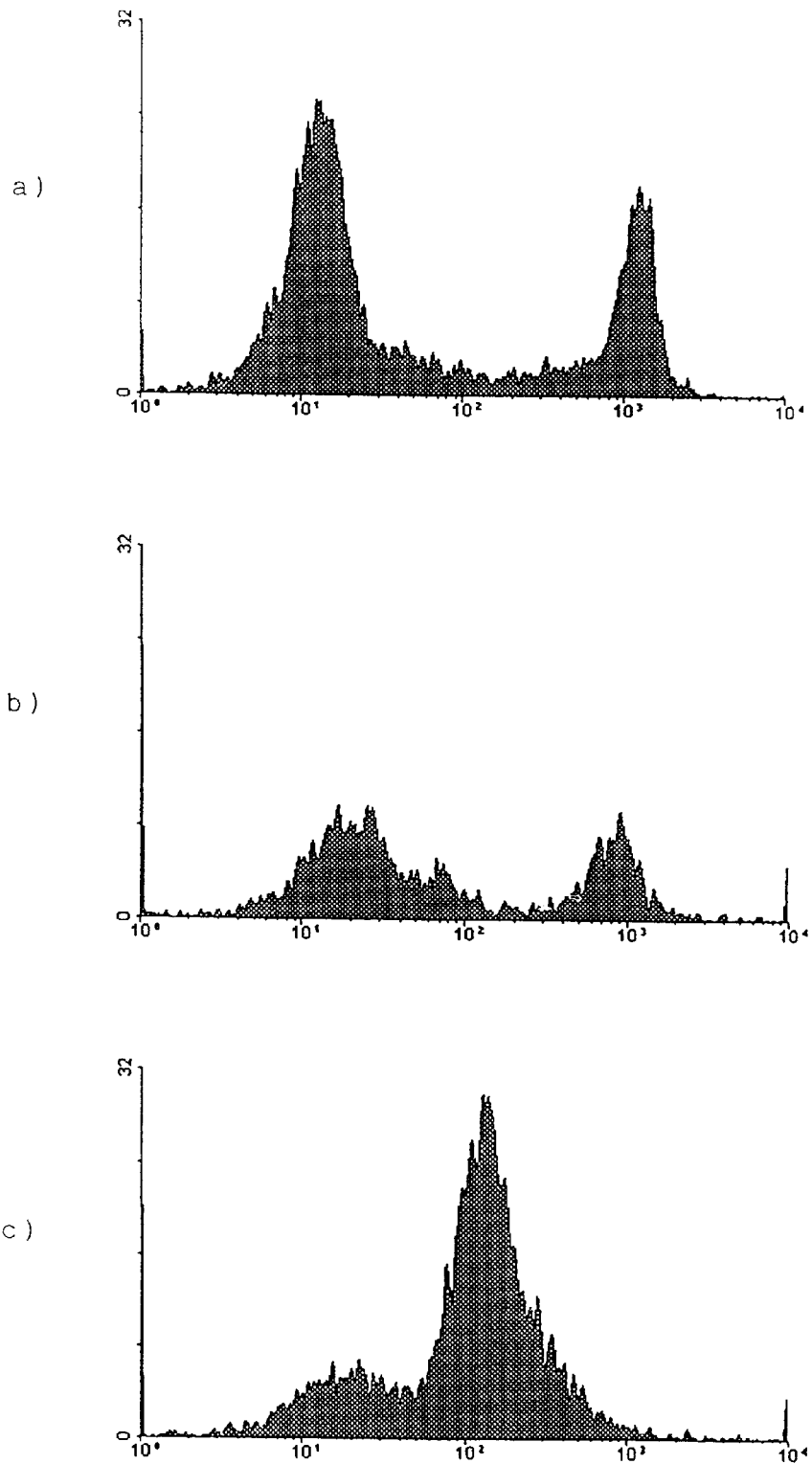
FIG. 6 shows the results of flow cytometry experiments described in Example 20. (Events against FL1LOG.)

Ficoll purified cells ($1 \times 10^6$ cells per sample) were incubated with anti-CD36 antibody for 30 min at room temperature, diluted (1:1000) in PBS/BSA. Cells were washed in PBS/BSA, and then incubated with an anti-mouse-HRP conjugate (1:1000 in PBS/BSA) for 30 min at room temperature. Cells were washed as before, and then treated with biotin tyramine at 12.5 μg/ml. Samples which were to receive just one biotin tyramine treatment were then washed and incubated with streptavidin-FITC (1:1000 in PBS/BSA). The samples which received a further treament of biotin tyramine were incubated with streptavidin-HRP (1:1000 in PBS/BSA) for 30 min at room temperature, then washed and treated with biotin tyramine as before. Cells were washed again, and then incubated with streptavidin-FITC as before.

b. Results Samples were analysed by flow cytometry and the fluorescence shifts overlayed, as shown in FIG. 5. As can be seen from the figure iteration of the biotin tyramine treament results in a 2.5 fold shift in the average fluorescence level of the cells. This is to expected given the observation that biotinylation may occurs over a range of up to 25 nm from the original site of HRP localisation Assuming the first biotin tyramine treatment biotinylates proteins in a circle of radius 25 nm from the HRP, then this would give an area of biotinylation of $\pi 25^2$ nM$^2$, which is 1963 nm$^2$. In the case of the second treatment with biotin tyramine the biotin desposited in this area is then saturated with streptavidin-HRP, so blocking binding of any streptavidin-FITC. The biotin tyramine treament is repeated giving a further area of biotinylation of $\pi 50^2 - \pi 25^2$, which is 5887 nm$^2$, which is an area three times the size of the original circle of biotin deposition. This fits with the experimentally observed observed fluorscence shift of around 2.5 fold.

The fluorescence shift observed after iterations of biotin tyramine treatment may be used to assess cellular copy numbers of cell surface proteins. If a protein is rare on a cell surface then the fluorescence signal should carry on is increasing with successive rounds of biotin tyramine treatment until the cell surface is saturated. If a protein is expressed at high copy number on a cell surface the fluorescence signal will saturate sooner because the circles of biotinylation will overlap.

EXAMPLE 20

Use of Biotin Tyramine to Specifically Biotinylate Subpopulations of Cells to Allow Their Subsequent Purification This example demonstrates using biotin tyramine to specifically biotinylate subpopulations of cells within a complex mix and then to capture the biotinylated cells to give an enriched population. The system chosen here uses an anti-CD36 mouse monoclonal antibody (Immunotech) which is a monocyte cell surface marker. A mixture of monocytes, lymphocytes and granulocytes was purified from blood on a Ficoll density gradient. Lymphocytes and granulocytes do not express CD36, hence the antibody should specifically biotinylate monocytes. The technique is equally applicable to any molecule which binds cell surfaces, and to any cell type, virus particle, bead or other population of particles displaying an sbp member or epitope.

a. Purification of cells from buffy coat.

Adult buffy coat blood from Cambridge Blood Transfusion Service was diluted 1:2 with Dulbeccos PBS (Tissue culture grade) then loaded onto 1077 density Ficoll Hypaque (Sigma). This was then spun at 1500 rpm for 30 min at room temperature with brake off. Cells at the interface were removed and washed once with PBS. Red cells were removed by using a whole blood erythrocyte lysing kit from R&D systems (Cat. no. WL1000). Cells were resuspended in 5 ml of lysing reagent and left for 5 min at room temperature then spun at 1000 rpm for 5 min and washed in 10 ml of wash reagent and again spun at 1000 rpm for 5 min. Cells were resuspended in PBS/0.5% BSA/2 mM EDTA (PBE) and then counted. In each of the following experiments $2.4 \times 10^6$ cells were used.

b. Antibody incubations and biotin tyramine treatment

Cells ($2.4 \times 10^6$) were incubated with mouse IgG, anti human CD36 antibody (Immunotech 0765) (2 $\mu$g/$10^5$ cells) for 30 minutes at 4–8° C., washed in PBE and spun at 1000 rpm for 5 min. Incubation with goat anti-mouse HRP conjugated antibody (1:1000 dilution) was the same as for the anti CD36 antibody. All antibodies were diluted in PBE. Cell pellets were resuspended in 100 $\mu$l of 50 mM Tris-HCl pH 7.4 with 2 $\mu$l biotin-tyramine (5 $\mu$g) and 1 $\mu$l of $H_2O_2$. This was left at room temperature for 10 minutes and then washed with 5 ml of PBE.

c. Capture of biotinylated cells

This was carried out using streptavidin MACS beads (Miltenyi Biotec) as per manufacturer's instructions. Cells from the previous treatment was resuspended in 80 $\mu$l PBE with 20 $\mu$l of MACS streptavidin (Cat no. 481-01). Incubation was for 15 min at 4° C. Cells were washed in PBE, resuspended in 100 $\mu$l of PBE and loaded onto a MACS column enclosed in a MASS magnet. Cells were allowed to run in to the column, and then the column was washed with $2 \times 1$ ml of PBE to remove unsound cells. Cells were eluted from the column by removing the column from the magnet, adding 1 ml of PBE, and then pushing the plunger into the reservoir to push the PBE through the column. Cells were eluted into an eppendorf and then spun at 4000 rpm for 5 min in a microcentrifuge. Cell pellets were resuspended in 80 $\mu$l of PBE and 20 $\mu$l of anti-CD36 antibody conjugated to fluorescein (Immunotech 0766). Cells were incubated in the dark at 4° C. for 20 minutes. Samples were then analysed by flow cytometry.

d. Results

Anti-CD36 antibody, followed by anti-mouse-HRP and biotin tyramine treatment was successful in biotinylating a subpopulation of cells which were subsequently captured on streptavidin beads. The captured cells were found to be CD36 positive and were at the appropriate position by forward and side scatter in the flow analysis to be monocytes (FIG. 9).

EXAMPLE 21

Figure 7:
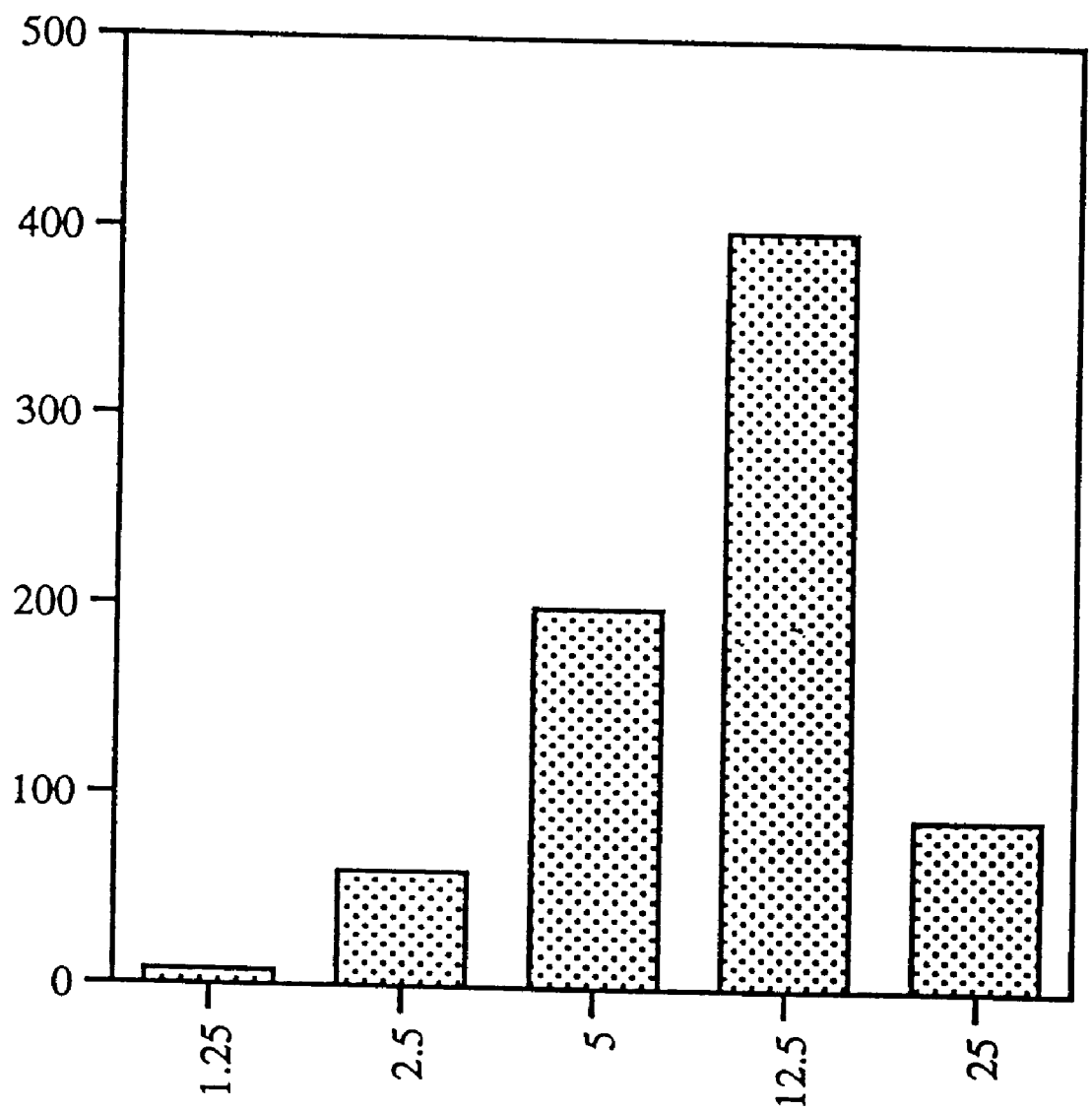
FIG. 7 shows the results of experiments described in Example 21. Phage recovered ($\times 10^5$) is plotted for various concentrations of biotin-tyramine in μg/ml.

Biotinylation of Phage Particles in Solution to Validate Biotin-Tyramine Preparations A phage preparation was made as described in Example 12 part a). Phage particles were diluted to a titre of $1 \times 10^9$ phage in 1 ml and 1 $\mu$l of a HRP-conjugated mouse Mab recognising the gene 8 protein HRP conjugate (Pharmacia) was added to the phage in solution. This was incubated at room temperature for 1 hr, and the phage were then treated with biotin tyramine, as described in Example 12 part b). Additional dilutions of biotin tyramine ranging from a 1:100 dilution of the normal stock solution, up to 100 fold excess over the normal concentrations remained constant. Biotinylated phage were then captured on 30 $\mu$l preblocked streptavidin-coated beads and the beads washed as described before. Phage captured on beads were titred and the optimal biotin tyramine concentration which gave maximal biotinylation was established. The results are shown in FIG. 7.

This provides a means of validating preparations of biotin tyramine, and allows comparison between different batches. The optimal biotin tyramine was evaluated for two different preparations of biotin tyramine, and was found to be comparable.

TABLE 1

| Expt. No. | Phage type | 1st Mab | 2nd Mab (HRP) (1/2500) | BT | No. phage in TEA eluate ($\times 10^5$) | No. phage recovered on beads ($\times 10^3$) | % Eluate recovered |
|---|---|---|---|---|---|---|---|
| (i) | CEA6 | 1/100 | + | + | 5.6 | 4400 | 0.80 |
| (ii) | CEA6 | 1/1000 | + | + | 3.9 | 1000 | 0.25 |
| (iii) | CEA6 | 1/10000 | + | + | 9.1 | 1500 | 0.16 |
| (iv) | CEA6 | 1/100 | + | − | 5.3 | 280 | 0.05 |
| (v) | CEA6 | 1/100 | − | + | 4.2 | 840 | 0.20 |
| (vi) | CEA6 | — | + | + | 4.6 | 440 | 0.10 |
| (vii) | OP1 | 1/100 | + | + | 1.8 | 80 | 0.04 |

TABLE 2

| Selection round No. | Round 1 phage taken | 1st Mab | No. phage in eluate (×10⁵) | No. phage recovered on beads (×10²) | % Eluate recovered |
|---|---|---|---|---|---|
| 1A | | 1/100 | 7.7 | >300 | >4 |
| 1B | | — | 3.4 | >200 | >6 |
| 2 | 1A | 1/100 | 1.8 | 4.13 | 0.23 |
| 2 | 1A | 1/1000 | 1.4 | 3.64 | 0.26 |
| 2 | 1B | — | 2.8 | 1.11 | 0.04 |
| 2 | 1A | — | 1.5 | 1.87 | 0.12 |

TABLE 4

| Clone | $lc_{off}$ (s$^{-1}$) |
|---|---|
| SS1A4 | 8.9 × 10$^{-2}$ |
| SS1A11 | 7.2 × 10$^{-2}$ |
| SS1G12 | 3.3 × 10$^{-2}$ |
| SS22A8 | 7.8 × 10$^{-2}$ |
| SS22B7 | 1.9 × 10$^{-2}$ |
| SS22B1 | 1.3 × 10$^{-2}$ |
| SS22D12 | 3.4 × 10$^{-2}$ |
| SS22E4 | 7.5 × 10$^{-2}$ |
| SS21B7 | 2.0 × 10$^{-2}$ |
| SSDS1 | 3.0 × 10$^{-2}$ |
| SS22A4 | ND |
| SS21B7 | ND |

TABLE 3

| Selection | Round 1 phage taken | No. Clones screened | CEA + ve | % CEA + ve |
|---|---|---|---|---|
| 1A | — | 94 | 3 | 4 |
| 1B | — | 94 | 0 | 0 |
| 2A | 1A | 48 | 13 | 27 |
| 2B | 1A | 65 | 11 | 17 |
| 2C | 1A | 48 | 4 | 8 |
| 2D | 1B | 25 | 1 | 4 |

1A = Selection with 1:100 dilution of anti-CEA mouse Mab
1B = Selection with no anti-CEA Mab present
2A = Selection 1A taken and subjected to a second round of selection in the presence of a 1:100 dilution of the anti-CEA mouse Mab
2B = Selection 1A taken and subjected to a second round of selection in the presence of a 1:1000 dilution of the anti-CEA mouse Mab
2C = Selection 1A taken and subjected to a second round of selection in the absence of the anti-CEA mouse Mab
2D = Selection 1B taken and subjected to a second round of selection in the absence of the anti-CEA mouse Mab

TABLE 5

| Selection | Round 1 phage taken | No. Clones screened | Mab + ve | % Mab + ve |
|---|---|---|---|---|
| 1A | — | 94 | 2 | 2 |
| 1B | — | 94 | 0 | 0 |
| 2A | 1A | 48 | 6 | 13 |
| 2B | 1A | 65 | 5 | 8 |
| 2C | 1A | 48 | 2 | 4 |
| 2D | 1B | 25 | 0 | 0 |

1A = Selection with 1:100 dilution of anti-CEA mouse Mab
1B = Selection with no anti-CEA Mab present
2A = Selection 1A taken and subjected to a second round of selection in the presence of a 1:100 dilution of the anti-CEA mouse Mab
2B = Selection 1A taken and subjected to a second round of selection in the presence of a 1:1000 dilution of the anti-CEA mouse Mab
2C = Selection 1A taken and subjected to a second round of selection in the absence of the anti-CEA mouse Mab
2D = Selection 1B taken and subjected to a second round of selection in the absence of the anti-CEA mouse Mab

We claim:

1. A method of obtaining one or more labeled proteins, peptides, or ligands, the method including
providing in a common medium:
label molecules;
a first marker ligand able to bind a member of a specific binding pair (sbp), which specific binding pair has a first sbp member and a second sbp member, and wherein said first marker ligand is able to bind said second sbp member;
a said second sbp member;
an enzyme able to catalyse binding of said label molecules to proteins, peptides or ligands, said enzyme being conjugated to said first marker ligand;
causing or allowing binding of said first marker ligand to said second sbp member;
causing or allowing binding of said label molecules to proteins, peptides or ligands in the vicinity of said first marker ligand bound to said second sbp member thereby providing labelled proteins, peptides or ligands; and
isolating and/or purifying said one or more labelled proteins, peptides or ligands from the medium.

2. A method according to claim 1 wherein said proteins, peptides or ligands to which said label molecule binds comprise a sbp member ("first sbp member") which binds said second sbp member.

3. A method according to claim 2 wherein said first sbp member is displayed on the surface of a virus particle and said particle is isolated and/or purified following binding of said first sbp member to said second sbp member and labelling of said particle and/or said first sbp member which is displayed on the surface of a virus particle.

4. A method according to claim 1 wherein said proteins, peptides or ligands to which said label molecule binds comprise a sbp member ("first sbp member") which binds a protein, peptide or ligand in the vicinity of said second sbp member.

5. A method according to claim 2 or claim 4 wherein a first sbp member labelled in accordance with the method is employed as a second marker ligand in a further performance of said method.

6. A method according to claim 5 wherein a protein, peptide or ligand labelled in accordance with said further performance of said method is isolated and/or purified from the medium.

7. A method according to claim 6 wherein said protein, peptide or ligand labelled in accordance with said further performance of said method is an agonist or antagonist of said first marker ligand.

8. A method according to claim 4 wherein said first sbp member is displayed on the surface of a virus particle, said label molecules bind to said virus particle and/or said first sbp member which is displayed on the surface of a virus particle, and said virus particle is isolated and/or purified following binding of said first sbp member to said protein, peptide or ligand in the vicinity of said second sbp member and labelling of said virus particle and/or said first sbp member which is displayed on the surface of a virus particle.

9. A method according to claim 1 wherein said label is a member of a further specific binding pair.

10. A method according to claim 9 wherein labelled proteins, peptides or ligands are isolated and/or purified by means of binding of said label to sbp member complementary to said label.

11. A method according to claim 9 wherein said label is biotin.

12. A method according to claim 11 wherein biotinylated protein, peptides, or ligands are isolated and/or purified by means of binding of biotin to streptavidin.

13. A method according to claim 1 wherein an isolated and/or purified protein, peptides or ligands is modified following its isolation and/or purification.

14. A method according to claim 13 wherein the isolated and/or purified protein, peptide or ligands is a peptide or polypeptide molecule and is modified by addition, insertion, substitution and/or deletion of one or more amino acids following isolation and/or purification of said peptide or polypeptide molecule.

15. A method according to claim 13 wherein the isolated and/or purified protein, peptide or ligands is modified by linkage of another molecule following isolation and/or purification of said isolated and/or purified molecule.

16. A method according to claim 1 wherein an isolated and/or purified protein, peptide or ligand or a derivative thereof is formulated into a composition which comprises at least one additional component.

17. A method according to claim 16 wherein said composition comprises a pharmaceutically acceptable vehicle or carrier.

18. A method according to claim 1 wherein said second sbp member is displayed on the surface of a virus particle and said particle is isolated and/or purified following binding of said first marker ligand to said second sbp member and labelling of said particle and/or said second sbp member which is displayed on the surface of a virus particle.

19. A method according to claim 18, claim 3 or claim 18 wherein said virus particle is isolated and/or purified by means of a member of a further specific binding pair able to bind said labelled virus particle and/or first or second sbp member which is displayed on the surface of a virus particle.

* * * * *

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 645 base pairs
      (B) TYPE: nucleic acid
      (C) STRANDEDNESS: double
      (D) TOPOLOGY: linear (xi) SEQUENCE DESCRIPTION: SEQ ID NO: 1:

```
GAATTCCGGA AAAAACAAAA TTCCTGTAAA ACAAATTAAC TCCAGGAACT TAAAATTTAC      60

TCCAAGACAT TTCCCTCAAA ACAAAGCAAA AAACCCCAGC AAAGATCGTT ACATCACAAA     120

ACCAAACACA AAGACCAGCG GTCACAGGCA AGTTCCTCTA AGCTTCCATT CTGCTGACTG     180

GTGGCTTCCA TTTAAAAGGA GTCTTTTAAT CAAGCCACTT TCACAGAATT TAAAACAAAC     240

CAAACACATG TAAATTGCAA AATACAAAAA GGTAAATTTA TAAGTAAAAA TGACCAAACC     300

CACAAAACTG GAGTATTTCG AAGGTTGAGG GTTCAGTGGA GGGTGTAACA CGAAAGGAAC     360

TTCACAACTG AAAGAAATCA TTGCCGAGTT TCCTCCAGGC AGCACTGAAA TGAATGGAGA     420

ACCTTCTCTC GAACATCTCA CACGTTAAAA AAAATAAATA TTTAAGAGAT ACAAGGCTCA     480
```

```
GATTGGTTTT CATATACATT GCACTTGAAG TTTAAGACCC AATACTTGCA AATTAGGTCT      540

GGTATGGTTT ATGCCATTAA ATGAATACAT TGTGCTCACC AATATCATTG ACTAGAAACA      600

CCACACGTTT AATGCAGTGC CATATGCAAT CTGTGACCGG AATTC                     645
```

(2) INFORMATION FOR SEQ ID NO: 2:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 2:

```
Glu Phe Arg Lys Lys Gln Asn Ser Cys Lys Thr Asn
1               5                   10
```

(2) INFORMATION FOR SEQ ID NO: 3:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO: 3:

```
Leu Gln Glu Leu Lys Ile Tyr Ser Lys Thr Phe Pro Ser Lys Gln Ser
1               5                   10                  15

Lys Lys Pro Gln Gln Arg Ser Leu His His Lys Thr Lys His Lys Asp
            20                  25                  30

Gln Arg Ser Gln Ala Ser Ser Lys Leu Pro Phe Cys
            35                  40              45
```

(2) INFORMATION FOR SEQ ID NO: 4:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 4:

```
Leu Val Ala Ser Ile
1               5
```

(2) INFORMATION FOR SEQ ID NO: 5:

(i) SEQUENCE CHARACTERISTICS:
        (A) LENGTH: 50 amino acids
        (B) TYPE: amino acid
        (D) TOPOLOGY: linear (xi) SEQUENCE DESCRIPTION: SEQ ID NO: 5:

```
Lys Glu Ser Phe Asn Gln Ala Thr Phe Thr Glu Phe Lys Thr Asn Gln
1               5                   10                  15

Thr His Val Asn Cys Lys Ile Gln Lys Gly Lys Phe Ile Ser Lys Asn
            20                  25                  30

Asp Gln Thr His Lys Thr Gly Val Phe Arg Arg Leu Arg Val Gln Trp
            35                  40                  45

Arg Val
    50
```

(2) INFORMATION FOR SEQ ID NO: 6:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO: 6:

His Glu Arg Asn Phe Thr Thr Glu Arg Asn His Cys Arg Val Ser Ser
1               5                   10                  15

Arg Gln His (2) INFORMATION FOR SEQ ID NO: 7:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 7:

Asn Glu Trp Arg Thr Phe Ser Arg Thr Ser His Thr Leu Lys Lys Ile
1               5                   10                  15

Asn Ile (2) INFORMATION FOR SEQ ID NO: 8:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO: 8:

Glu Ile Gln Gly Ser Asp Trp Phe Ser Tyr Thr Leu His Leu Lys Phe
1               5                   10                  15

Lys Thr Gln Tyr Leu Gln Ile Arg Ser Gly Met Val Tyr Ala Ile Lys
                20                  25                  30

(2) INFORMATION FOR SEQ ID NO: 9:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 9:

Ile His Cys Ala His Gln Tyr His
1               5

(2) INFORMATION FOR SEQ ID NO: 10:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 10:

Leu Glu Thr Pro His Val
1               5

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 11:

Cys Ser Ala Ile Cys Asn Leu
1               5

(2) INFORMATION FOR SEQ ID NO: 12:

(i) SEQUENCE CHARACTERISTICS:
    (A) LENGTH: 83 amino acids
    (B) TYPE: amino acid
    (D) TOPOLOGY: linear (xi) SEQUENCE DESCRIPTION: SEQ ID NO: 12:

Asn Ser Gly Lys Asn Lys Ile Pro Val Lys Gln Ile Asn Ser Arg Asn
1               5                   10                  15

Leu Lys Phe Thr Pro Arg His Phe Pro Gln Asn Lys Ala Lys Asn Pro
            20                  25                  30

Ser Lys Asp Arg Tyr Ile Thr Lys Pro Asn Thr Lys Thr Ser Gly His
        35                  40                  45

Arg Gln Val Pro Leu Ser Phe His Ser Ala Asp Trp Trp Leu Pro Phe
    50                  55                  60

Lys Arg Ser Leu Leu Ile Lys Pro Leu Ser Gln Asn Leu Lys Gln Thr
65                  70                  75                  80

Lys His Met (2) INFORMATION FOR SEQ ID NO: 13:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 13:

Ile Ala Lys Tyr Lys Lys Val Asn Leu
1               5

(2) INFORMATION FOR SEQ ID NO: 14:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 14:

Val Lys Met Thr Lys Pro Thr Lys Leu Glu Tyr Phe Glu Gly
1               5                   10

(2) INFORMATION FOR SEQ ID NO: 15:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO: 15:

Gly Phe Ser Gly Gly Cys Asn Thr Lys Gly Thr Ser Gln Leu Lys Glu
1               5                   10                  15

Ile Ile Ala Glu Phe Pro Pro Gly Ser Thr Glu Met Asn Gly Glu Pro
            20                  25                  30

Ser Leu Glu His Leu Thr Arg
        35

(2) INFORMATION FOR SEQ ID NO: 16:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 16:

```
Ile Phe Lys Arg Tyr Lys Ala Gln Ile Gly Phe His Ile His Cys Thr
1               5                   10                  15
```

(2) INFORMATION FOR SEQ ID NO: 17:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO: 17:

```
Ser Leu Arg Pro Asn Thr Cys Lys Leu Gly Leu Val Trp Phe Met Pro
1               5                   10                  15

Leu Asn Glu Tyr Ile Val Leu Thr Asn Ile Ile Asp
                20                  25
```

(2) INFORMATION FOR SEQ ID NO: 18:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 18:

```
Lys His His Thr Phe Asn Ala Val Pro Tyr Ala Ile Cys Asp Arg Asn
1               5                   10                  15
```

(2) INFORMATION FOR SEQ ID NO: 19:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 19:

```
Ile Pro Glu Lys Thr Lys Phe Leu
1               5
```

(2) INFORMATION FOR SEQ ID NO: 20:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 20:

```
Asn Lys Leu Thr Pro Gly Thr
1               5
```

(2) INFORMATION FOR SEQ ID NO: 21:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO: 21:

```
Asn Leu Leu Gln Asp Ile Ser Leu Lys Thr Lys Gln Lys Thr Pro Ala
1               5                   10                  15

Lys Ile Val Thr Ser Gln Asn Gln Thr Gln Arg Pro Ala Val Thr Gly
                20                  25                  30

Lys Phe Leu
        35
```

(2) INFORMATION FOR SEQ ID NO: 22:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 22:

Ala Ser Ile Leu Leu Thr Gly Gly Phe His Leu Lys Gly Val Phe
1               5                   10                  15

(2) INFORMATION FOR SEQ ID NO: 23:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 23:

Ser Ser His Phe His Arg Ile
1               5

(2) INFORMATION FOR SEQ ID NO: 24:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 24:

Asn Lys Pro Asn Thr Cys Lys Leu Gln Asn Thr Lys Arg
1               5                   10

(2) INFORMATION FOR SEQ ID NO: 25:

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO: 25:

Pro Asn Pro Gln Asn Trp Ser Ile Ser Lys Val Glu Gly Ser Val Glu
1               5                   10                  15

Gly Val Thr Arg Lys Glu Leu His Asn
                20                  25

(2) INFORMATION FOR SEQ ID NO: 26:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 26:

Lys Lys Ser Leu Pro Ser Phe Leu Gln Ala Ala Leu Lys
1               5                   10

(2) INFORMATION FOR SEQ ID NO: 27:

(i) SEQUENCE CHARACTERISTICS:
        (A) LENGTH: 33 amino acids
        (B) TYPE: amino acid
        (D) TOPOLOGY: linear (xi) SEQUENCE DESCRIPTION: SEQ ID NO: 27:

Met Glu Asn Leu Leu Ser Asn Ile Ser His Val Lys Lys Asn Lys Tyr
1               5                   10                  15

Leu Arg Asp Thr Arg Leu Arg Leu Val Phe Ile Tyr Ile Ala Leu Glu

Val (2) INFORMATION FOR SEQ ID NO: 28:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 28:

Asp Pro Ile Leu Ala Asn
1           5

(2) INFORMATION FOR SEQ ID NO: 29:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 29:

Val Trp Tyr Gly Leu Cys His
1           5

(2) INFORMATION FOR SEQ ID NO: 30:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO: 30:

Met Asn Thr Leu Cys Ser Pro Ile Ser Leu Thr Arg Asn Thr Thr Arg
1           5               10              15

Leu Met Gln Cys His Met Gln Ser Val Thr Gly Ile
           20              25

(2) INFORMATION FOR SEQ ID NO: 31:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 31:

Gly Gly Gly Gly Ser Gly Gly Gly Gly Ser Gly Gly Gly Gly Ser
1           5               10              15

(2) INFORMATION FOR SEQ ID NO: 32:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO: 32:

Met Asp Tyr Gln Val Ser Ser Pro Ile Tyr Asp Ile Asn Tyr Tyr Thr
1           5               10              15

Ser Glu Pro Cys
           20

(2) INFORMATION FOR SEQ ID NO: 33:

(i) SEQUENCE CHARACTERISTICS:
        (A) LENGTH: 10 amino acids
        (B) TYPE: amino acid -continued

```
        (D) TOPOLOGY: linear (xi) SEQUENCE DESCRIPTION: SEQ ID NO: 33:

Pro Met Pro His Ala Glu Gly Lys Ser Thr
1               5                   10

(2) INFORMATION FOR SEQ ID NO: 34:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 34:

Gly Ala Ala Glu Gln Lys Leu Ile Ser Glu Glu Asp Leu Met
1               5                   10

(2) INFORMATION FOR SEQ ID NO: 35:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 35:

GACTCCTGGA GCCCG                                                    15

(2) INFORMATION FOR SEQ ID NO: 36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 36:

CGCGGCCAGC GATGG                                                    15
```